US011584949B2

(12) United States Patent
Georgiou et al.

(10) Patent No.: US 11,584,949 B2
(45) Date of Patent: *Feb. 21, 2023

(54) ENGINEERED ENZYMES WITH METHIONINE-GAMMA-LYASE ENZYMES AND PHARMACOLOGICAL PREPARATIONS THEREOF

(71) Applicant: AEMASE, INC., Austin, TX (US)

(72) Inventors: George Georgiou, Austin, TX (US); Everett Stone, Austin, TX (US)

(73) Assignee: AEMASE, INC., Austin, TX (US)

( * ) Notice: Subject to any disclaimer, the term of this patent is extended or adjusted under 35 U.S.C. 154(b) by 290 days.

This patent is subject to a terminal disclaimer.

(21) Appl. No.: 16/691,418

(22) Filed: Nov. 21, 2019

(65) Prior Publication Data

US 2020/0087706 A1    Mar. 19, 2020

Related U.S. Application Data

(60) Continuation of application No. 15/887,276, filed on Feb. 2, 2018, now Pat. No. 10,526,638, which is a division of application No. 15/052,978, filed on Feb. 25, 2016, now Pat. No. 9,909,163, which is a division of application No. 14/225,518, filed on Mar. 26, 2014, now Pat. No. 9,279,119, which is a division of application No. 13/020,268, filed on Feb. 3, 2011, now Pat. No. 8,709,407.

(60) Provisional application No. 61/301,368, filed on Feb. 4, 2010.

(51) Int. Cl.
| | |
|---|---|
| C12Q 1/527 | (2006.01) |
| C12N 9/88 | (2006.01) |
| C12N 9/96 | (2006.01) |
| C12Q 1/10 | (2006.01) |
| A61K 38/00 | (2006.01) |

(52) U.S. Cl.
CPC ............... *C12Q 1/527* (2013.01); *C12N 9/88* (2013.01); *C12N 9/96* (2013.01); *C12Q 1/10* (2013.01); *A61K 38/00* (2013.01); *G01N 2333/988* (2013.01)

(58) Field of Classification Search
CPC .................................................... C12Q 1/527
See application file for complete search history.

(56) References Cited

U.S. PATENT DOCUMENTS

| | | | |
|---|---|---|---|
| 4,870,287 A | 9/1989 | Cole et al. | |
| 5,739,169 A | 4/1998 | Ocain et al. | |
| 5,760,395 A | 6/1998 | Johnstone | |
| 5,824,311 A | 10/1998 | Greene et al. | |
| 5,830,880 A | 11/1998 | Sedlacek et al. | |
| 5,846,945 A | 12/1998 | McCormick | |
| 5,889,155 A | 3/1999 | Ashkenazi et al. | |
| 8,709,407 B2 * | 4/2014 | Georgiou ................. | C12Q 1/10 435/232 |
| 9,279,119 B2 | 3/2016 | Georgiou et al. | |
| 9,481,877 B2 | 11/2016 | Georgiou et al. | |
| 9,624,484 B2 | 4/2017 | Georgiou et al. | |
| 9,909,163 B2 | 3/2018 | Georgiou et al. | |
| 2004/0110164 A1 | 6/2004 | Inagaki et al. | |
| 2005/0036981 A1 | 2/2005 | Yagi et al. | |
| 2005/0036984 A1 | 2/2005 | Harrison et al. | |
| 2006/0107342 A1 | 5/2006 | Amir | |
| 2006/0275279 A1 | 12/2006 | Rozzell et al. | |
| 2009/0304666 A1 | 12/2009 | Harrison et al. | |
| 2011/0200576 A1 | 8/2011 | Georgiou et al. | |
| 2012/0156672 A1 | 6/2012 | Otte et al. | |
| 2014/0287484 A1 | 9/2014 | Georgiou et al. | |
| 2015/0064159 A1 | 3/2015 | Georgiou et al. | |
| 2015/0064160 A1 | 3/2015 | Georgiou et al. | |
| 2018/0002685 A1 | 1/2018 | Georgiou et al. | |
| 2018/0008681 A1 | 1/2018 | Stone | |

FOREIGN PATENT DOCUMENTS

| | | |
|---|---|---|
| JP | 2007-500696 A | 1/2007 |
| JP | 2013-518594 A | 5/2013 |
| WO | WO-2002/020807 A1 | 3/2002 |
| WO | WO-2003106971 A2 | 12/2003 |
| WO | WO-2005045055 A2 | 5/2005 |
| WO | WO-2011097381 A2 | 8/2011 |
| WO | WO-2015031726 A2 | 3/2015 |
| WO | WO-2015031735 A1 | 3/2015 |
| WO | WO-2018009663 A1 | 1/2018 |

OTHER PUBLICATIONS

"Macaca fascicularis," Genbank ID No. AAW71993, Jan. 7, 2005.
"Pan troglodytes," Genbank ID No. XP_513486, May 13, 2011.
"Pongo abelii cystathionase (cystathionine gamma-lyase) (CTH), mRNA," Database DDBJ/EMBL/GeneBank [online], Accession No. NM_001131163, available at: http:www.ncbi.nlm.nih.gov/nuccore/197098155?sat=13&satkey=11125499, dated Aug. 20, 2008.
"Pongo abelii," Genbank ID No. NP_001124635, Mar. 10, 2011.
Ashe et al., "N5-methyltetrahydrofolate: homocysteine methyltransferase activity in extracts from normal, malignant and embryonic tissue culture cells," *Biochem. Biophys. Res. Common.*, 57:417-25, 1974.
Breillout et al., In: Methionine dependency of malignant tumors: a possible approach for therapy, Oxford University Press, 1628-1632, 1990.
Breitinger et al., "The three-dimensional structure of cystathionine β-lyase from Arabidopsis and its substrate specificity," *Plant Physiology*, 126:631-42, 2001.
Esaki and Soda, "L-methionine gamma-lyase from Pseudomonas putida and Aeromonas," *Methods Enzymol.*, 143:459-65, 1987.

(Continued)

*Primary Examiner* — Scott Long
(74) *Attorney, Agent, or Firm* — Servilla Whitney LLC

(57) ABSTRACT

Methods and composition related to the engineering of a novel protein with methionine-γ-lyase enzyme activity are described. For example, in certain aspects there may be disclosed a modified cystathionine-γ-lyase (CGL) comprising one or more amino acid substitutions and capable of degrading methionine. Furthermore, certain aspects of the invention provide compositions and methods for the treatment of cancer with methionine depletion using the disclosed proteins or nucleic acids.

19 Claims, 9 Drawing Sheets

Specification includes a Sequence Listing.

(56) References Cited

OTHER PUBLICATIONS

Halpern et al., "The effect of replacement of methionine by homocystine on survival of malignant and normal adult mammalian cells in culture," *Proc. Natl. Acad. Sci.*, 71:113-1136, 1974.
Hori et al., "Gene cloning and characterization of Pseudomonas putida L-methionine-alpha-deamino-gamma-mercaptomethane-lyase," *Cancer Res.*, 56:2116-22, 1996.
Huang et al., "Site-directed mutagenesis on human cysthionine-gamma-lyase reveals insights into the modulation of H2S production," *Journal of Molecular Biology*, 396(3):708-718, 2009.
Ito et al., "Purification and characterization of methioninase from Pseudomonas putida," *J. Biochem.*, 79:1263-72, 1976.
Kraus et al., "Cystathionine γ-lyase: clinical, metabolic, genetic, and structural studies," *Mol. Genet. Metab.*, 97:250-9, 2009.
Kreis and Goodenow, "Methionine requirement and replacement by homocysteine in tissue cultures of selected rodent and human malignant and normal cells," *Cancer Res.*, 38:2259-62, 1978.
Kreis et al., "Effect of nutritional and enzymatic methionine deprivation upon human normal and malignant cells in tissue culture," *Cancer Res.*, 40:634-41, 1980.
Kreis, "Tumor therapy by deprivation of L-methionine: rationale and results," *Cancer Treatment Rpts.*, 63:1069-72, 1979.
Kudou et al., "Structure of the antitumour enzyme L-methionine gamma-lyase from Pseudomonas putida at 1.8 A resolution," *J. Biochem.*, 141:535-44, 2007.
Lishko et al., "Depletion of serum methionine by methioninase in mice," *Anticancer Res.*, 13:1465-8, 1993.
Liu et al., "Methionine dependency and the therapy of tumor," *Parenteral and Enteral Nutrition*, 12(4): 247-250-, 2005. (English Abstract).
Lu et al., "Cloning and nucleotide sequence of human liver cDNA encoding for cystathionine gamma-lyase," *Biochem. Biophys.Res. Common.*, 189:749-58, 1992 (Abstract only).
Messerschmidt et al., "Determinants of enzymatic specificity in the Cys-Met-metabolism PLP-dependent enzymes family: crystal structure of cystathionine gamma-lyase from yeast and intrafamilar structure comparison," *Biol. Chem.*, 384:373-86, 2003.
Motoshima et al., "Crystal structure of the pyridoxal 5'-phospate dependent L-methionine gamma-lyase from Pseudomaonas putida," *J. Biochem.*, 128(3):349-354, 2000.
Nakayama et al., "Purification of bacterialk L-methionine gamma-lyase," *Anal. Biochem.*, 138:421-4, 1984.
Office Communication issued in Australian Patent Application No. 2011212885, dated Oct. 27, 2014.
Office Communication issued in Chinese patent application No. 201180013307, dated Mar. 29, 2013. (English translation of Chinese text).
Office Communication issued in Chinese Patent Application No. 20118001307, dated Oct. 25, 2013. (English translation of Chinse text).
Office Communication issued in Chinese Patent Application No. 201180013307, dated Apr. 9, 2014. (English translation of Chinese test).
Office Communication issued in Japanese Patent Application No. 2012-552084, dated Mar. 12, 2015. (English translation of Japanese text).
Office Communication issued in Japanese Patent Application No. 2012-552084, dated Aug. 24, 2015. (English translation of Japanese text).
Office Communication issued in U.S. Appl. No. 13/020,268, dated Jun. 18, 2013.
Office Communication issued in U.S. Appl. No. 13/020,268, dated Dec. 11, 2012.
PCT International Search Report and Written Opinion, issued in International Application No. PCT/US2011/023606, dated Oct. 25, 2011.
Rao et al., "Role of the transsulfuration pathway and of gammy-cystathionase activity in the formation of cysteine and sulfate from methionine in rat hepatocyts," *J. Nutrition*, 120:837-45, 1990.

Response to the Office Communication submitted in corresponding U.S. Appl. No. 13/020,268, dated Oct. 9, 2013.
Sato and Nozaki, "Methionine gamma-lyase: the unique reaction mechanism, physiological roles, and therapeutic applications against infectious diseases and cancers," *IUMBM Life*, 61:1019-28, 2009.
Schellenberger et al., "A recombinant polypeptide extends the in vivo half-life of peptides and proteins in a tunable manner," *Nat. Biotechnol.*, 27:1186-90, 2009.
Sridhar et al., "Crystallization and preliminary crystallographic characterization of recombinant L-methionine-alpha-deamino-gamma-mercapomethane lyase (methininase)," *Acta. Crystall. Section D Biol. Crystall*, 56:1665-7, 2000.
Steegborn et al.,"Kinetics and inhibition of recombinant human cystathionine gamma-lyase. Toward the rational control of transsulfuration," *J. Biolog. Chem.*,274:12675-84, 1999.
Stone et al., "De novo engineering of a human cystathionine-γ-lyase for systemic (L)-Methionine depletion cancer therapy," *ACS Chem Biol.*, 7(11): 1822-1829, 2012.
Sun et al., "In vivo efficacy of recombinant methioninase is enhanced by the combination of polyethylene glycol conjugation and pyridoxal 5'-phospate supplementation," *Cancer Research*, 63:8377-8383, 2003.
Tan et al., "Anticancer efficacy of methioninase in vivo," *Anticancer Res.*, 16:3931-6, 1996.
Tan et al., "Overexpression and large-scale production of recombinant L-methionine-alpha-deamino-gamma-mercaptomethane-lyase for novel anticancer therapy," *Protein Expr. Purif.*, 9:233-45, 1997.
Tan et al., "Recombinant methioninase infusion reduces the biochemical endpoint of serum methionine with minimal toxicity in high-stage cancer patients," *Anticancer Res.*, 17:3857-60, 1997.
Tan et al., "Serum methionine depletion without side effects by methioninase in metastatic breast cancer patients," *Anticancer Res.*, 16:3937-42, 1996.
Wawrzynczak and Thorpe, In: Immunoconjugates, Antibody Conjugates In Radioimaging and Therapy of Cancer,Vogel (Ed.), NY, Oxford University Press, pp. 28-55, 1987.
Yang et al., "PEGylation confers greatly extended half-life and attenuated immunogenicity to recombinant methioninase inprimates," *Cancer Research*, 64:6673-8, 2004.
Yange et al., "Pharmacokinetics, methionine depletion, and antigenicity of recombinant methioninase in primates," *Clinical Cancer Research*, 10:2131-8, 2004.
Yoshioka et al., "Anticancer efficacy in vivo and in vitro, synergy with 5-fluorouracil, and safety of recombinant methioninase," *Cancer Res.*, 58:2583-7, 1998.
Zhu et al., "Kinetic properties of polymorphic variants and pathogenic mutants in human cystathionin γ-lyase," *Biochemistry*, 47:6226-32, 2008.
N.M. Antikainen et al., "Altering protein specificity: techniques and applications", *Bioorganic & Medicinal Chemistry*, 13:2701-2716 (2005).
O. Khersonsky et al., "Enzyme promiscuity: evolutionary and mechanistic aspects", Current Opinion in Chemical Biology 10:498-508 (2006).
A. Goyer et al. "Functional Characterization of a Methionine gamma-Lyase in *Arabidopsis* and its implication in an Alternative to the Reverse Tans-sulfuration Pathway", *Plant Cell Physiol.*, 48(2):232-242 (2007).
"Cystathionine gamma-lyase [Rattus norvegicus]," Genbank ID No. BAB19922.2, Apr. 20, 2001.
"Cystathionine gamma-lyase homolog [imported]—Stenotrophomonas maltophilia," Genbank ID No. T45483, Jan. 31, 2000.
"Google Search—wei-cheng lu evolved enzymes for cancer therapeutics and orthogonal system," dated Jan. 18, 2017.
"Human recombinant Fc fused protein," Funakoshi News, Mar. 1, 2013.
"Hypothetical protein [Pongo abelii]," Genbank ID No. CAH89476.1, May 1, 2008.
Bahr et al., "Q5RFI1_PONAB," seuqence submitted Dec. 21, 2004, and retrieved on Dec. 10, 2018.
Cramer et al., "Systemic depletion of L-cyst(e)ine with cyst(e)inase increases reactive oxygen species and suppresses tumor growth," *Nat. Med.* (2016): 21:120-127.

(56) References Cited

OTHER PUBLICATIONS

Doxsee et al., "Sulfasalazine-induced cystine starvation: Potential use for prostate cancer therapy," (2007): *The Prostate*, 67:162-171.
Ercolani et al., "Bladder outlet obstruction in male cystinuria mice," *Int. Urol. Nephrol.* (2010): 42:57-63.
Feliubadalo et al., "Slc7a9-deficient mice develop cystinuria non-I and cystine urolithiasis" (2003): *Hum. Mol. Genet.*, 12:2097-2108.
Glode et al., "Cysteine auxotrophy of human leukemic lymphoblasts is associated with decreased amounts of intracellular cystathionase protein," *Biochemistry* (1981): 20(5):1306-1311.
Guan et al., "The x c—cystine/glutamate antiporter as a potential therapeutic target for small-cell lung cancer: use of sulfasalazine," *Cancer Chemotherapy & Pharmacology* (2009): 64(3):463-472.
Kim et al., "Expression of cystathionine β-synthase is downregulated in hepatocellular carcinoma and associated with poor prognosis," *Oncology Reports* (2009): 21(6):1449-1454.
Knoll et al., "Cystinuria in childhood and adolescence: recommendations for diagnosis, treatment, and follow-up," *Pediatric Nephrology* (2004): 20(1):19-24.
Link et al., "Cystathionase: a potential cytoplasmic marker of hematopoietic differentiation," *Blut* (1983): 47(1):31-39.
Livrozet et al., "An animal model of Type A Cystinuria due to spontaneous mutation in 129S2/SvPasCrl Mice" (2014): *PLoS ONE*, 9:e102700.
Lu, Wei-Cheng, "Evolved enzymes for cancer therapeutics and orthogonal system," *Dissertation—The University of Texas at Austin* (Aug. 2013).
Mudd et al., "Homocystinuria: an enzymatic defect," *Science* (1964): 143:1443-1445.
Nygård et al., "Major lifestyle determinants of plasma total homocysteine distribution: the Hordaland Homocysteine Study," *The American Journal of Clinical Nutrition* (1998): 67:263-270.
Paley, Olga M., "Engineering a novel human methionine degrading enzyme as a broadly effective cancer therapeutic," *Dissertation—The University of Texas at Austin* (Aug. 2014).
Peters et al., "A mouse model for cystinuria type I," *Hum. Mol. Genet.* (2003): 12:2109-2120.
Stone et al., "Strategies for optimizing the serum persistence of engineered human arginase I for cancer therapy," *Journal of Controlled Release* (2012): 158:171-179.
Stone et al., "De Novo Engineering of a Human Cystathionine-γ-Lyase for Systemic (L)-Methionine Depletion Cancer Therapy," *ACS Chem. Biol.* (2012): 7(11):1822-1829 [Supporting Information].
Takakura et al., "Assay method for antitumor L-methionine γ-lyase: comprehensive kinetic analysis of the complex reaction with L-methionine," *Analytical Biochemistry* (2004): 327(2):233-240.
Tiziani et al., "Optimized metabolite extraction from blood serum for 1H nuclear magnetic resonance spectroscopy," *Analytical Biochemistry* (2008): 377:16-23.
Tiziani et al., "Metabolomics of the tumor microenvironment in pediatric acute lymphoblastic leukemia" (2013): *PLoS ONE*, 8:e82859.
Walter et al. "Strategies for the treatment of cystathionine beta-synthase deficiency: the experience of the Willink Biochemical Genetics Unit over the past 30 years," *European Journal of Pediatrics* (1998); 157:S71-S76.
Yan et al., "Structural Snapshots of an Engineered Cystathionine-[gamma]-lyase Reveal the Critical Role of Electrostatic Interactions in the Active Site," Biochemistry (2017): 56(6): 876-885.
Zhang et al., "Stromal control of cysteine metabolism promotes cancer cell survival in chronic lymphocytic leukemia" (2012): *Nat. Cell Biol.*, 14:276-286.
Zhao et al., "Frequent Epigenetic Silencing of the Folate-Metabolising Gene Cystathionine-Beta-Synthase in Gastrointestinal Cancer," *PLoS ONE* (2012): 7(11):e49683.
Office Communication issued in U.S. Appl. No. 14/472,750, dated Dec. 31, 2015.
Office Communication issued in U.S. Appl. No. 14/472,779, dated Jun. 2, 2015.
Office Communication issued in U.S. Appl. No. 14/472,779, dated Oct. 28, 2015.
Office Communication issued in U.S. Appl. No. 15/052,978, dated Jul. 6, 2017.
Office Communication issued in U.S. Appl. No. 15/451,349, dated Jul. 16, 2018.
Extended European Search Report issued in European Application No. 14841106.9, dated Jan. 30, 2017.
Extended European Search Report issued in European Application No. 11740355.0, dated Feb. 26, 2019.
International Search Report and Written Opinion issued in International Application No. PCT/US2017/040897, dated Oct. 10, 2017.
International Search Report and Written Opinion issued in International Application No. PCT/US2014/053359, dated Mar. 23, 2015.
International Search Report and Written Opinion issued in International Application No. PCT/US2014/053374, dated Jan. 14, 2015.
Invitation to Pay Additional Fees issued in International Application No. PCT/US2014/053359, dated Jan. 16, 2015.
Office Communication issued in Australian Patent Application No. 2014312159, dated Aug. 10, 2018.
Extended European Search Report issued in European Patent Application No. 14839001.6, dated Feb. 17, 2017.
Office Communication issued in European Patent Application No. 14839001.6, dated Mar. 5, 2018.
Office Communication issued in Japanese Patent Application No. 2016-537882, dated Aug. 9, 2018.
Office Communication issued in Japanese Patent Application No. 2016-537886, dated Jun. 20, 2018.
Office Communication issued in Canadian Application No. 2,788,689, dated Dec. 27, 2017.
International Search Report and Written Opinion issued in International Application No. PCT/US2018/032286, dated Jul. 6, 2018.
International Search Report and Written Opinion issued in International Application No. PCT/US2018/032246, dated Aug. 1, 2018.
Response to Office Communication issued in Chinese Patent Application No. 201180013307, dated Jul. 29, 2013 [Partial Translation].
Response to Office Communication issued in Chinese Patent Application No. 201180013307, dated Dec. 5, 2013.
Office Communication issued in Israel Patent Application No. 244263, dated Sep. 16, 2018.
Partial European Search Report for EP11740355.0, dated Nov. 22, 2018.
Office Communication issued in Chinese Patent Application No. 201480050681.0, dated Mar. 11, 2019 (English translation of Chinese text).
Office Communication issued in Japanese Patent Application No. 2016-537886, dated Mar. 13, 2019 (English translation of Japanese text).
Office Communication issued in Chinese Patent Application No. 201480054224.9, dated Jan. 3, 2019 (English translation of Chinese text).
Office Communication issued in European Patent Application No. 2014839001, dated Mar. 5, 2018.
"Probable cystathionine gamma-lyase PA0400 [imported]—Pseudomonas aeruginosa," Genbank ID No. F83595, Sep. 15, 2000.

\* cited by examiner

| Inhibition of in vitro proliferation of NB cells | | |
|---|---|---|
| | PEG-hCGL-NLV | pMGL |
| Cell lines | IC50 (U) Average of 2 exp. | IC50 (U) Average of 2 exp. |
| BE(1)N | 0.039 ± 0.009 | 0.042 ± 0.007 |
| BE(2)N | 0.076 ± 0.004 | 0.074 ± 0.008 |
| BE(2)S | 0.076 ± 0.035 | 0.075 ± 0.038 |
| BE(2)C | 0.063 ± 0.004 | 0.061 ± 0.005 |
| SK-N-LD | 0.074 ± 0.021 | 0.100 ± 0.050 |
| NMB-7 | 0.067 ± 0.018 | 0.080 ± 0.021 |
| SH-EP-1 | 0.151 ± 0.054 | 0.174 ± 0.086 |
| IMR32 | 0.051 ± 0.002 | 0.043 ± 0.005 |
| CHP-212 | 0.175 ± 0.077 | 0.137 ± 0.065 |
| SKN-MM | 0.161 ± 0.052 | 0.111 ± 0.054 |
| LAN-1 | 0.075 ± 0.020 | 0.053 ± 0.006 |
| LAI-66N | 0.068 ± 0.003 | 0.088 ± 0.025 |
| LAI-55N | 0.073 ± 0.004 | 0.072 ± 0.003 |
| LAI-5S | 0.123 ± 0.035 | 0.099 ± 0.012 |
| $IC_{50}$ (half maximal inhibitory concentration) was expressed as mean ± SD | | |

FIG. 8

ENGINEERED ENZYMES WITH METHIONINE-GAMMA-LYASE ENZYMES AND PHARMACOLOGICAL PREPARATIONS THEREOF

This application is a continuation of co-pending U.S. patent application Ser. No. 15/887,276, filed Feb. 2, 2018 (now allowed), which is a divisional U.S. patent application Ser. No. 15/052,978, filed Feb. 25, 2016 (now U.S. Pat. No. 9,909,163, issued Mar. 6, 2018), which is a divisional of U.S. patent application Ser. No. 14/225,518, filed Mar. 26, 2014 (now U.S. Pat. No. 9,279,119, issued Mar. 8, 2016), which is a divisional of U.S. patent application Ser. No. 13/020,268, filed Feb. 3, 2011 (now U.S. Pat. No. 8,709,407, issued Apr. 29, 2014), which claims priority to U.S. Provisional Patent Application No. 61/301,368, filed Feb. 4, 2010. The entire contents of each of the above referenced disclosures are specifically incorporated herein by reference.

This invention was made with government support under Grant no. R01 CA139059 and R01 CA154754 awarded by the National Institutes of Health. The government has certain rights in the invention.

BACKGROUND OF THE INVENTION

The instant application contains a sequence listing qhich has been submitted in ASCII format via EFS-Web and is hereby incorporated by reference in its entirety. Said ASCII copy, created on Nov. 19, 2019, is named 218107_003_04_594513_US_SL.txt and is 45,327 bytes in size.

1. Field of the Invention

The invention generally relates to compositions and methods for the treatment of cancer with enzymes that deplete L-Methionine. More particularly, it concerns the engineering of a novel human methionine-γ-lyase enzyme with methionine degrading activity and greatly enhanced stability suitable for human therapy.

2. Description of Related Art

The demand for the essential amino acid, methionine, is exceptionally high in cancerous tissues. Depletion of methionine has been shown to be effective in killing a wide variety of tumor types without adversely effecting non-cancerous tissues. Methionine depletion can be effected via the action of enzymes that hydrolyze the amino acid. While human methionine depleting enzymes do not exist, a bacterial enzyme from *Pseudomonas aeruginosa,* methionine-γ-lyase, has been shown to be therapeutically effective in the clinic and has been evaluated in clinical trials. However, methionine-γ-lyase, as a bacterial protein, is highly immunogenic and elicits the formation of specific antibodies, leading to adverse reactions and reduced activity. Methionine-γ-lyase also has a very short half-life of only ~2 hrs in vitro and in vivo, necessitating very frequent and impractically high dosing to achieve systemic depletion.

Systemic methionine depletion is the focus of much research and has the potential to treat cancers such as metastatic breast cancer, prostate, neuroblastoma, and pancreatic carcinoma among others. Although there is a lot of excitement for this therapeutic approach, the bacterially derived methionine-γ-lyase has serious shortcoming which greatly dampens enthusiasm for it as a chemotherapeutic agent.

Thus, there remains a need to develop methods and compositions to address these shortcomings for the therapeutic success of L-methionine depletion therapy.

SUMMARY OF THE INVENTION

Certain aspects of the present invention overcome a major deficiency in the art by providing novel enzymes that comprise human polypeptide sequences having methionine-γ-lyase (MGL) activity, which may be suitable for cancer therapy and have low immunogenicity and improved serum stability. Accordingly, in a first embodiment there is provided a modified polypeptide, particularly a novel enzyme variant with methionine degrading activity derived from primate enzymes related to MGL. For example, the novel enzyme variant may have an amino acid sequence selected from the group consisting of SEQ ID NO: 10-17. In particular, the variant may be derived from human enzymes such as human cystathionine-γ-lyase (CGL). In certain aspects, there may be a polypeptide comprising a modified human cystathionine gamma-lyase capable of degrading methionine. In some embodiments, the polypeptide may be capable of degrading methionine under physiological conditions. For example, the polypeptide may have a catalytic efficiency for methionine ($k_{cat}/K_M$) of at least or about 0.01, 0.05, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$ $M^{-1}s^{-1}$ or any range derivable therein. In further aspects, the polypeptide may display a catalytic activity towards L-homocystine up to $k_{cat}/K_M$ of 100, 95, 90, 85, 80, 75, 70, 65, 60, 55, 50, 45, 40, 35, 30, 25, 20, 15, 10, 9, 8, 7, 6, 5, 4, 3, 2, 1, 0.9, 0.8, 0.7, 0.6, 0.5, 0.4, 0.3, 0.2, 0.1, 0.05, 0.01, 0.005, 0.001 $M^{-1}s^{-1}$ or any range derivable therein.

A modified polypeptide as discussed above may be characterized as having a certain percentage of identity as compared to an unmodified polypeptide (e.g., a native polypeptide) or to any polypeptide sequence disclosed herein. For example, the unmodified polypeptide may comprise at least or up to about 10, 20, 30, 40, 50, 60, 70, 80, 90, 100, 150, 200, 250, 300, 350, 400 residues (or any range derivable therein) of a native primate cystathionase (i.e., cystathionine gamma lyase). The percentage identity may be about, at most or at least 50%, 55%, 60%, 65%, 70%, 75%, 80%, 85%, 90%, 95%, 96%, 97%, 98%, 99% or 100% (or any range derivable therein) between the modified and unmodified polypeptides, or between any two sequences in comparison. It is also contemplated that percentage of identity discussed above may relate to a particular modified region of a polypeptide as compared to an unmodified region of a polypeptide. For instance, a polypeptide may contain a modified or mutant substrate recognition site of cystathionase that can be characterized based on the identity of the amino acid sequence of the modified or mutant substrate recognition site of cystathionase to that of an unmodified or mutant cystathionase from the same species or across the species. A modified or mutant human polypeptide characterized, for example, as having at least 90% identity to an unmodified cystathionase means that 90% of the amino acids in that modified or mutant human polypeptide are identical to the amino acids in the unmodified polypeptide.

Such an unmodified polypeptide may be a native cystathionase, particularly a human isoform or other primate isoforms. For example, the native human cystathionase may have the sequence of SEQ ID NO:1. Non-limiting examples of other native primate cystathionases include *Pongo abelii* cystathionase (Genbank ID: NP_001124635.1; SEQ ID NO:18), *Macaca fascicularis* cystathionase (Genbank II): AAW71993.1; SEQ ID NO:19), and *Pan troglodytes* cystathionase (Genbank ID: XP_513486.2; SEQ ID NO: 20). Exemplary native polypeptides include a sequence having about, at most or at least 50%, 55%, 60%, 65%, 70%, 75%, 80%, 85%, 90%, 95%, 96%, 97%, 98%, 99% or 100% identity (or any range derivable therein) of SEQ ID NO:1 or 18-20 or a fragment thereof. For example, the native polypeptide may comprise at least or up to about 10, 20, 30, 40, 50, 60, 70, 80, 90, 100, 150, 200, 250, 300, 350, 400, 415 residues (or any range derivable therein) of the sequence of SEQ ID NO:1 or 18-20.

In some embodiments, the native cystathionine gamma-lyase may be modified by one or more other modifications such as chemical modifications, substitutions, insertions, deletions, and/or truncations. For example, the modifications may be at a substrate recognitions site of the native enzyme. In a particular embodiment, the native cystathionine may be modified by substitutions. For example, the number of substitutions may be one, two, three, four or more. In further embodiments, the native cystathionine gamma-lyase may be modified in the substrate recognition site or any location that may affect substrate specificity. Particularly, the amino acids that may be modified are charged residues, such as negatively charged (e.g., Asp, Asn) or positive charged residues (e.g., Arg, Lys). For example, the modified polypeptide may have the at least one amino acid substitution at amino acid positions corresponding to E59, E119 and/or R339 of SEQ ID NO:1 or amino acid positions of 59, 119 and/or 339 of a primate cystathionine gamma-lyase. For example, the primate may be human. *Pongo abelii, Macaca fascicularis, Pan Troglodyte.*

In certain embodiments, the modifications may be substitutions of one or more charged residues (including positively charged residues such as Arg or R, Lys or K, His or H and negatively charged residues such as Asp or D and Glu or E) with neutral residues (e.g., Ala, Asn, Gin, Gly, Ile, Leu, or Val). For example, the substitutions at amino acid positions 59, 119 and/or 339 is an aspartic acid (N), a valine (V), or a leucine (L). In particular embodiments, the modification are one or more substitutions selected from the group consisting of E59N, E59V, R119L, and E339V. In a further embodiment, the substitutions may comprise a R119L and E339V substitutions. In a still further embodiment, the substitutions may comprise an additional substitutions of E59N or E59V.

In some embodiments, the native cystathionine-γ-lyase may be a human cystathionine-γ-lyase. In a particular embodiment, the substitutions are a combination of E59N, R119L, and E339V of human cystathionine gamma-lyase (for example, the modified polypeptide having the amino acid sequence of SEQ ID NO:10, a fragment or homolog thereof) or a combination of E59V, R119L, and E339V of human cystathionine gamma-lyase (for example, the modified polypeptide having the amino acid sequence of SEQ ID NO:11, a fragment or homolog thereof). In a further embodiment, the modified polypeptide may be *Pongo abelii Pongo abelii* CGL-NLV mutant (SEQ ID NO:12), *Pongo abelii* CGL-VLV mutant (SEQ ID NO:13); *Macaca fascicularis* CGL-NLV mutant (SEQ ID NO:14), *Macaca fascicularis* CGL-VLV mutant (SEQ ID NO:15); *Pan Troglodytes* CGL-NLV mutant (SEQ ID NO:16), and *Pan Troglodytes* CGL-VLV mutant (SEQ ID NO:17).

In some aspects, the present invention also contemplates polypeptides comprising the modified cystathionine gamma-lyase linked to a heterologous amino acid sequence. For example, the modified cystathionine gamma-lyase may be linked to the heterologous amino acid sequence as a fusion protein. In a particular embodiment, the modified cystathionine gamma-lyase may be linked to an XTEN polypeptide for increasing the in vivo half-life.

To increase serum stability, the modified cystathionine gamma-lyase may be linked to one or more polyether molecules. In a particular embodiment, the polyether may be polyethylene glycol (PEG). The modified polypeptide may be linked to PEG via its specific amino acid residues, such as lysine or cysteine. For therapeutical administration, such a polypeptide comprising the modified cystathionine gamma-lyase may be dispersed in a pharmaceutically acceptable carrier.

In some aspects, a nucleic acid encoding such a modified cystathionine gamma-lyase is contemplated. In some embodiments, the nucleic acid has been codon optimized for expression in bacteria. In particular embodiments, the bacteria is *E. coli*. In other aspects, the present invention further contemplates vectors such as expression vectors containing such nucleic acids. In particular embodiments, the nucleic acid encoding the modified cystathionine gamma-lyase is operably linked to a promoter, including but not limited to heterologous promoters.

In still further aspects, the present invention further contemplates host cells comprising such vectors. The host cells may be bacteria, such as *E. coli* To further differentiate desired CGL mutants with methionine degrading activity from the native cystathionine gamma-lyase, host cells having deletions of ilvA and metA (e.g., *E. coli* ilvA-metA-) may be prepared and used to identify desired mutants.

In a further embodiment, there may be also provided a method of of identifying a primate cystathionine gamma-lyase variant having L-methionine degrading activity, comprising: a) expressing a population of primate cystathionine gamma-lyase variants in cells of an *E. coli* strain having deletions of genes ilvA and metA, wherein the variant comprises at least one amino acid substitution as compared to a native primate cystathionine gamma-lyase; and b) identifying a primate cystathionine gamma-lyase variant having L-methionine degrading activity, wherein cells expressing the identified variant has a higher growth rate in a minimal medium supplemented with L-methionine as compared to cells expressing the native primate cystathionine gamma-lyase in otherwise identical conditions.

In some embodiments, the vectors are introduced into host cells for expressing the modified cystathionine gamma lyase. The proteins may be expressed in any suitable manner. In one embodiment, the proteins are expressed in a host cell such that the protein is glycosylated. In another embodiment, the proteins are expressed in a host cell such that the protein is aglycosylated.

Certain aspects of the present invention also contemplate methods of treatment by the administration of the modified cystathionine gamma-lyase peptide, the nucleic acid, or the formulation of the present invention, and in particular methods of treating tumor cells or subjects with cancer. The subject may be any animal such as mouse. For example, the subject may be a mammal, particularly a primate, and more particularly a human patient. In some embodiments, the method may comprise selecting a patient with cancer. In certain aspects, the subject or patient may be maintained on a methionine-restricted diet or a normal diet.

In some embodiments, the cancer is any cancer that is sensitive to methionine depletion. In one embodiment, the present invention contemplates a method of treating a tumor cell or a cancer patient comprising administering a formulation comprising such a polypeptide. In some embodiments, the administration occurs under conditions such that at least a portion of the cells of the cancer are killed. In another embodiment, the formulation comprises such a modified cystathionine gamma-lyase with methionine degrading activity at physiological conditions and further comprising an attached polyethylene glycol chain. In some embodiment, the formulation is a pharmaceutical formulation comprising any of the above discussed cystathionine gamma-lyase variants and pharmaceutically acceptable excipients. Such pharmaceutically acceptable excipients are well known to those having skill in the art. All of the above cystathionine gamma-lyase variants may be contemplated as useful for human therapy.

In a further embodiment, there may also be provided a method of treating a tumor cell comprising administering a formulation comprising a non-bacterial (mammalian, e.g., primate or mouse) modified cystathionine gamma-lyase that has methionine degrading activity or a nucleic acid encoding thereof.

Because tumor cells are dependent upon their nutrient medium for methionine, the administration or treatment may be directed to the nutrient source for the cells, and not necessarily the cells themselves. Therefore, in an in vivo application, treating a tumor cell includes contacting the nutrient medium for a population of tumor cells with the engineered methioninase. In this embodiment, the medium can be blood, lymphatic fluid, spinal fluid and the like bodily fluid where methionine depletion is desired.

In accordance with certain aspects of the present invention, such a formulation containing the modified cystathionine gamma-lyase can be administered intravenously, intradermally, intraarterially, intraperitoneally, intralesionally, intracranially, intraarticularly, intraprostaticaly, intrapleurally, intrasynovially, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularly, orally, topically, by inhalation, infusion, continuous infusion, localized perfusion, via a catheter, via a lavage, in lipid compositions (e.g., liposomes), or by other method or any combination of the forgoing as would be known to one of ordinary skill in the art.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein in the specification, "a" or "an" may mean one or more. As used herein in the claim(s), when used in conjunction with the word "comprising", the words "a" or "an" may mean one or more than one.

The use of the term "of" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8: A Met(-)Hcyss(-)Chl(-) diet was fed to athymic mice before administration of 200 U PEG-hCGL-NLV (N=5). Serum methionine concentration was expressed as mean±SD. Blood methionine level decreased to a nadir of 3.9±0.7 μmol/L at 8 hours.

*p<0.01 when the treatment of PEG-hCGL-NLV in combination with Met(-)Hcyss(-)Chl(-) mouse feed was compared with other two groups.

Figure 11:
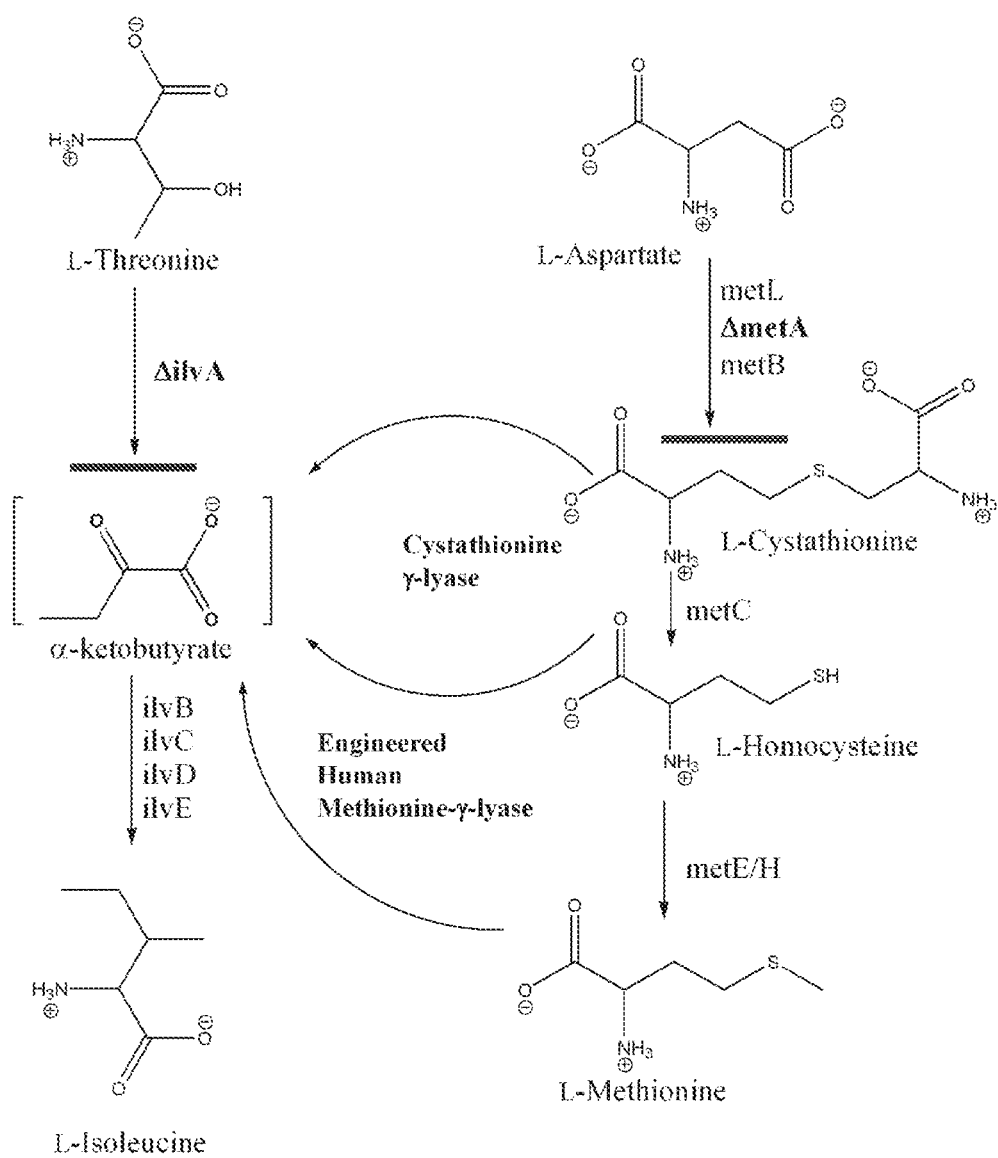

FIG. 11: Schematic of E. coli L-methionine and L-isoleucine synthetic pathways showing a double deletion of genes ilvA and metA. This renders E. coli auxotrophic for L-Met and L-Ile. If E. coli are grown on media supplemented with L-Met and harbor a gene encoding an active methionine-γ-lyase the resulting α-ketobutyrate production will compensate for the L-Ile auxotrophy.

Figure 12:
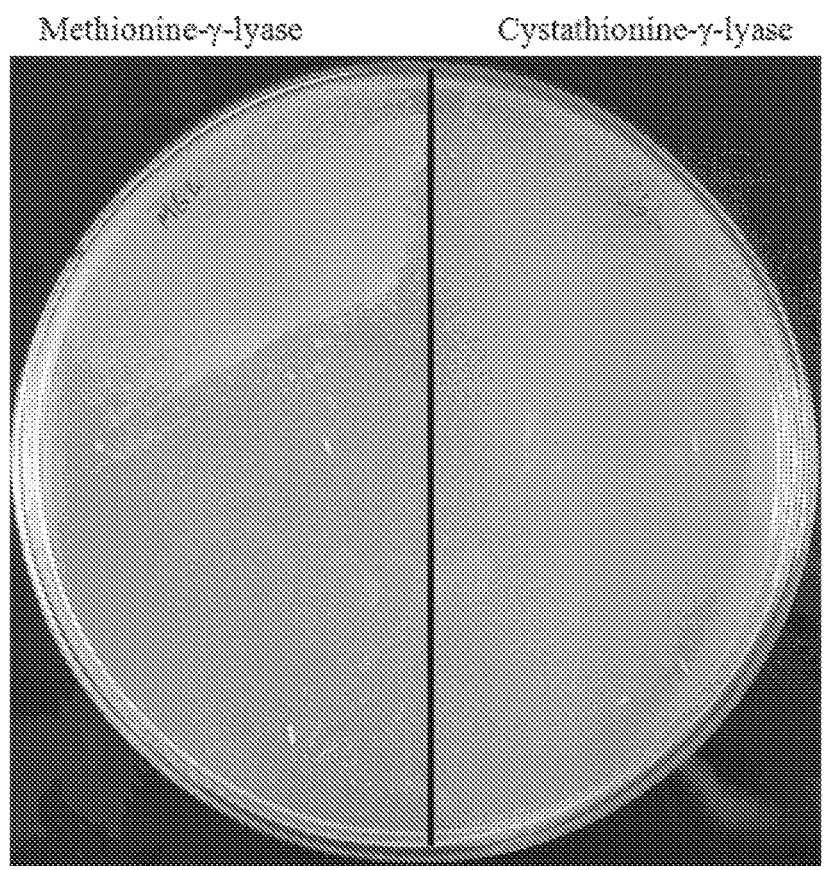

FIG. 12: E. coli BL:21(DE3) (ΔilvA ΔmetA) plated on M9 minimal media agar supplemented with 0.5 mil L-methionine and containing either a plasmid encoding a gene for methionine-γ-lyase (left) or a gene encoding a cystathionine-γ-lyase (right). Only MGL activity is able to rescue the L-isoleucine auxotrophy.

DESCRIPTION OF ILLUSTRATIVE EMBODIMENTS

The present disclosure, according to certain embodiments, is generally directed to compositions and methods for preparing a novel human enzyme engineered to have methionine degrading activity and its related therapeutic applications.

Without wishing to be bound by theory or mechanism, the present disclosure is based on the following studies. A high throughput assay was first developed for detecting methionine-γ-lyase by monitoring the formation of the product α-keto butyrate in 96 well plates and a second assay was also developed to rapidly determine enzyme kinetics following formation of methane thiol. A genetic selection for L-methione degradation activity was devised, based on the formation of α-ketobutyrate by the enzymes which in turn rescues the growth of E. coli ilvA mutant cells. Furthermore, saturation mutagenesis and random mutagenesis followed by high throughput screening for methionine degradation were performed to isolate cystathionine-γ-lyase variants with high methionine-γ-lyase activity.

As used herein the terms "protein" and "polypeptide" refer to compounds comprising amino acids joined via peptide bonds and are used interchangeably.

As used herein, the term "fusion protein" refers to a chimeric protein containing proteins or protein fragments operably linked in a non-native way.

As used herein, the term "half life" (½-life) refers to the time that would be required for the concentration of a polypeptide thereof to fall by half in vitro or in vivo, for example, after injection in a mammal.

The terms "in operable combination," "in operable order" and "operably linked" refer to a linkage wherein the components so described are in a relationship permitting them to function in their intended manner, for example, a linkage of nucleic acid sequences in such a manner that a nucleic acid molecule capable of directing the transcription of a given gene and/or the synthesis of desired protein molecule, or a linkage of amino acid sequences in such a manner so that a fusion protein is produced.

By the term "linker" is meant to refer to a compound or moiety that acts as a molecular bridge to operably link two different molecules, wherein one portion of the linker is operably linked to a first molecule, and wherein another portion of the linker is operably linked to a second molecule.

The term "pegylated" refers to conjugation with polyethylene glycol (PEG), which has been widely used as a drug carrier, given its high degree of biocompatibility and ease of modification. PEG can be coupled (e.g., covalently linked) to active agents through the hydroxy groups at the end of the PEG chain via chemical methods; however, PEG itself is limited to at most two active agents per molecule. In a different approach, copolymer of PEG and amino acids have been explored as novel biomaterial which would retain the biocompatibility of PEG, but which would have the added advantage of numerous attachment points per molecule (thus providing greater drug loading), and which can be synthetically designed to suit a variety of applications.

The term "gene" refers to a DNA sequence that comprises control and coding sequences necessary for the production of a polypeptide or precursor thereof. The polypeptide can be encoded by a full length coding sequence or by any portion of the coding sequence so as the desired enzymatic activity is retained.

The term "native" refers to the typical form of a gene, a gene product, or a characteristic of that gene or gene product when isolated from a naturally occurring source. A native form is that which is most frequently observed in a nature population and is thus arbitrarily designated the normal or wild-type form. In contrast, the term "modified," "variant," or "mutant" refers to a gene or gene product which displays modification in sequence and functional properties (i.e., altered characteristics) when compared to the native gene or gene product.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The term "therapeutically effective" as used herein refers to an amount of cells and/or therapeutic composition (such as a therapeutic polynucleotide and/or therapeutic polypeptide) that is employed in methods to achieve a therapeutic effect, such as wherein at least one symptom of a condition being treated is at least ameliorated, and/or to the analysis of the processes or materials used in conjunction with these cells.

The term "$K_M$" as used herein refers to the Michaelis-Menten constant for an enzyme and is defined as the concentration of the specific substrate at which a given enzyme yields one-half its maximum velocity in an enzyme catalyzed reaction. The term "$k_{cat}$" as used herein refers to the turnover number or the number of substrate molecule each enzyme site converts to product per unit time, and in which the enzyme is working at maximum efficiency. The term "$k_{cat}/K_M$" as used herein is the specificity constant which is a measure of how efficiently an enzyme converts a substrate into product.

The term "cystathionine-γ-lyase" (CGL or cystathionase) refers to any enzyme that catalyzes the hydrolysis of cystathionine to cysteine. For example, it include primate forms of cystathionine-γ-lyase, or particularly, human forms of cystathionine-γ-lyase.

I. Methionine-γ-Lyase and Cystathionine-γ-Lyase

A lyase is an enzyme that catalyzes the breaking of various chemical bonds, often forming a new double bond or a new ring structure. For example, an enzyme that catalyzed this reaction would be a lyase: ATP→cAMP+PP$_i$. Lyases differ from other enzymes in that they only require one substrate for the reaction in one direction, but two substrates for the reverse reaction.

A number of pyrioxal-5'-phosphate (PLP)-dependent enzymes are involved in the metabolism of cysteine, homocysteine, and methionine, and these enzymes form an evolutionary related family, designated as Cys/Met metabolism PLP-dependent enzymes. These enzymes are proteins of about 400 amino acids and the PLP group is attached to a lysine residue located in the central location of the polypeptide. Members of this family include cystathionine-γ-lyase (CGL), cystathionine-γ-synthase (CGS), cystathione-β-lyase (CBL), methionine-γ-lyase (MGL), O-acetylhomoserine (OAH)/O-acetyl-serine (OAS) sulfhydrylase (OSHS). Common to all of them is the formation of a Michaelis complex leading to an external substrate aldimine. The further course of the reaction is determined by the substrate specificity of the particular enzyme.

For example, the inventors introduced specific mutations into a PLP-dependent lyase family member such as the human cystathionine-γ-lyase to change its substrate specificity. In this manner the inventors produced novel variants with the de novo ability to degrade L-Met as a substrate. In other embodiments, a modification of other PLP-dependent enzymes for producing novel methionine degrading activity may also be contemplated.

As a PLP-dependent enzyme, a methionine gamma-lyase (EC 4.4.1.11) is an enzyme that catalyzes the chemical reaction: L-methionine+H$_2$O ⇌ methanethiol+NH$_3$+2-oxobutanoate. Thus, the two substrates of this enzyme are L-methionine and H$_2$O, whereas its 3 products are methanethiol, NH3, and 2-oxobutanoate. This enzyme belongs to the family of lyases, specifically the class of carbon-sulfur lyases. The systematic name of this enzyme class is L-methionine methanethiol-lyase (deaminating 2-oxobutanoate-forming). Other names in common use include L-methioninase, methionine lyase, methioninase, methionine dethiomethylase, L-methionine gamma-lyase, and L-methionine methanethiol-lyase (deaminating). This enzyme participates in selenoamino acid metabolism. It employs one cofactor, pyridoxal-5'-phosphate.

Methioninase usually consists of 389-441 amino acids and forms a homotetramer. Methioninase enzymes are generally composed of four identical subunits of molecular weight of ~45 kDa (Sridhar et at., 2000; Nakamura et at., 1984). The structure of the enzyme was elucidated by crystallization (Kudou et al., 2007). Each segment of the tetramer is composed of three regions: an extended N-terminal domain (residues 1-63) that includes two helices and three beta-strands, a large PLP binding domain (residues 64-262) which is made up of a mostly parallel seven stranded beta-sheet that is sandwiched between eight alpha-helices, and a C-terminal domain (residues 263-398). The cofactor PLP is required for catalytic function. Amino acids important for catalysis have been identified based on the structure. Tyr59 and Arg61 of neighboring subunits, which are also strongly conserved in other c-family enzymes, contact the phosphate group of PLP. These residues are important as the main anchor within the active site. Lys240, Asp241 and Arg61 of one monomer and Tyr114 and Cys116 of an adjacent monomer form a hydrogen-bond network in the methioninase active site that confers specificity to the enzyme.

Cystathionine gamma-lyase (CGL or cystathionase) is an enzyme which breaks down cystathionine into cysteine and α-ketobutyrate. Pyridoxal phosphate is a prosthetic group of this enzyme. Although mammals do not have a methioninase (MGL), they do have cystathionase with sequence, structural, and chemical homology to the bacterial MGL enzymes. As shown in Examples, protein engineering was used to convert cystathionase which has no activity for the degradation of L-Methione into an enzyme that can degrade this amino acid at a high rate.

II. Methioninase Engineering

Since humans do not produce methione-γ-lyase (MGL or methioninase) it is necessary to engineer methioninases for human therapy that have high activity and specificity for degrading methionine under physiological conditions, as well as high stability in physiological fluids such as serum and are also non-immunogenic because they are native proteins which normally elicit immunological tolerance.

Due to the undesired immunogenicity effects seen in the animal studies with pMGL, it is desirable to engineer L-methionine degradation activity in a human enzyme. Immunological tolerance to human proteins makes it likely that such an enzyme will be non-immunogenic or minimally immunogenic and therefore well tolerated.

Figure 1:
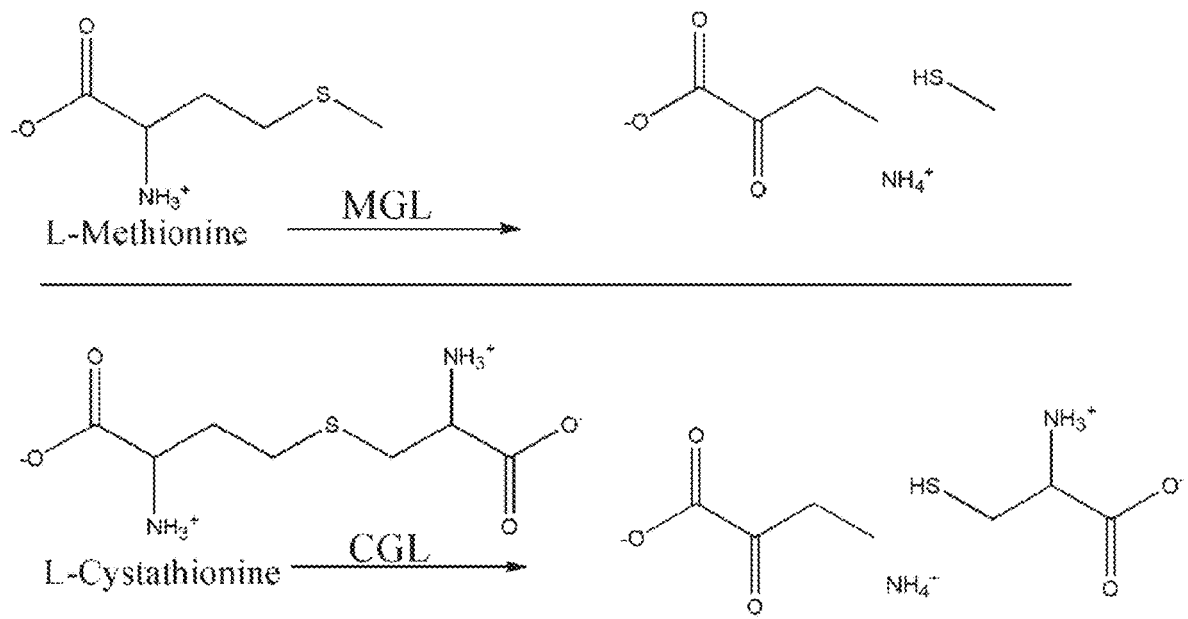
FIG. 1: CGL and MGL catalyze a similar PLP dependent degradation of L-cystathionine or L-Methionine (L-Met) into ammonia, α-ketobutyrate, and cysteine or methanethiol respectively.

Certain aspects of novel enzymes with MGL activity as engineered methioninase address these needs. Although mammals do not have a MGL, they do have a cystathionine-gamma-lyase (CGL) that has sequence, structural, and chemical homology to the bacterial MGL enzymes. CGL is a tetramer that catalyzes the last step in the mammalian transsulfuration pathway (Rao et al., 1990). CGL catalyzes the conversion of L-cystathionine to L-cysteine, alpha-ketobutyrate, and ammonia (FIG. 1). The human CGL (hCGL) cDNA had previously been cloned and expressed, but with relatively low yields (~5 mg/L culture) (Lu et al., 1992; Steegborn et al., 1999).

For example, there have been provided methods and compositions related to a primate (particularly human) cystathionine-γ-lyase (CGL or cystathionase) modified via mutagenesis to hydrolyze methionine with high efficiency, while the cystathionine-γ-lyase does not exhibit methioninase activity in its native form.

Some embodiments concern modified proteins and polypeptides. Particular embodiments concern a modified protein or polypeptide that exhibits at least one functional activity that is comparable to the unmodified version, preferably, the methioninase enzyme activity. In further aspects, the protein or polypeptide may be further modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide, such as the methioninase enzyme activity. In certain embodiments, the unmodified protein or polypeptide is a native cystathionine-γ-lyase, specifically a human cystathionine-γ-lyase. It is specifically contemplated that embodiments concerning a "modified protein" may be implemented with respect to a "modified polypeptide," and vice versa.

Determination of activity may be achieved using assays familiar to those of skill in the art, particularly with respect to the protein's activity, and may include for comparison purposes, for example, the use of native and/or recombinant versions of either the modified or unmodified protein or polypeptide. For example, the methioninase activity may be determined by any assay to detect the production of any substrates resulting from conversion of methionine, such as alpha-ketobutyrate, methanethiol, and/or ammonia.

In certain embodiments, a modified polypeptide, such as a modified cystathionine-γ-lyase, may be identified based on its increase in methionine degrading activity. For example, substrate recognition sites of the unmodified polypeptide may be identified. This identification may be based on structural analysis or homology analysis. A population of mutants involving modifications of such substrate recognitions sites may be generated. In a further embodiment, mutants with increased methionine degrading activity may be selected from the mutant population. Selection of desired mutants may include methods such as detection of byproducts or products from methionine degradation.

In a particular embodiment, there may be provided a method using an engineered strain of *E. coli* comprising chromosomal deletions of genes ilvA and metA such that an auxotrophic requirement of L-isoleucine and L-methionine exists. When media supplemented with L-methionine is provided in the presence of a plasmid encoding a methionine gamma lyase or an engineered cystathionine gamma-lyase having methionine degrading activity (but not native cystathionine gamma lyase), it may allow rescue of the L-isoleucine auxotrophy through production of α-ketobutyrate. The method may facilitate the identification of mutants with methionine degrading activity by minimizing the effect from other pathways that could also produce α-ketobutyrate.

Modified proteins may possess deletions and/or substitutions of amino acids; thus, a protein with a deletion, a protein with a substitution, and a protein with a deletion and a substitution are modified proteins. In some embodiments these modified proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to seine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A modified protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

III. Enzymatic L-Methionine Depletion for Therapy

In certain aspects, the polypeptides may be used for the treatment of diseases including cancers that are sensitive to methionine depletion such as hepatocellular carcinoma, melanoma, and renal cell carcinoma, with novel enzymes that deplete L-Methionine. The invention specifically discloses treatment methods using modified cystathionine-γ-lyase with methionine degrading activity. As described below, as currently available methionine-γ-lyases are typically bacterially-derived proteins, there remain several problems for their use in human therapy. Certain embodiments of the present invention provide novel enzymes with methionine-γ-lyase activity for increased therapeutic efficacy.

Methionine (L-Met) depletion has long been studied as a potential treatment for cancer. While L-Met is an essential amino acid, many malignant human cell lines and tumors have been shown to have a relatively greater requirement for methionine (Halpern et al., 1974; Kreis and Goodenow, 1978; Breiout et al., 1990; Kreis et al., 1980; Kreis, 1979). Methionine-dependent tumor cell lines present no or low levels of methionine synthase, the enzyme that normally recycles homocysteine back to L-Met (Halpern et al., 1974; Ashe et at., 1974). Most normal cells can grow on precursors like homocysteine and homocystine, whereas many malignant cells must scavenge L-Met directly from their extracellular environment. Also, any rapidly growing neoplasm can be adversely affected by the lack of essential building blocks necessary for growth. Methionine is particularly important as its depletion leads not only to diminished protein synthesis, but also dysregulates S-adenosylmethionine (SAM) dependent methylation pathways, which are particularly important for gene regulation.

The differences in methionine requirement between normal and cancer cells provide a therapeutic opportunity. Enzymatic methionine depletion has been explored in a number of animal model studies as well as phase I clinical trials (Tan et al., 1997a; Tan et al., 1996a; Lishko et al., 1993; Tan et al., 1996b; Yoshioka et al., 1998; Yang et al., 2004a; Yang et al., 2004b; Tan et al., 1997b).

Because humans lack a methionine hydrolyzing enzyme, bacterial L-methionine-gamma-lyases, MGL, from various sources have been evaluated for cancer therapy. Methionine-gamma-lyase catalyzes the conversion of methionine to methanethiol, alpha-ketobutyrate, and ammonia. Bacterial enzymes from various sources have been purified and tested as methionine depleting agents against cancer cell lines. The P. putida (pMGL) source was selected for therapeutic applications due to its high catalytic activity, low $K_M$ and a relatively high $k_{cat}$ value (Esaki and Soda, 1987; Ito et al., 1976), in comparison to other sources. Furthermore, the gene for pMGL has been cloned into E. coli and the protein was expressed at a high protein yield (Tan et al., 1997a; Hori et al., 1996).

In vivo studies have been performed on animal models, as well as humans. Tan et al. performed studies with human tumors xenografted in nude mice and found that lung, colon, kidney, brain, prostate, and melanoma cancers were all sensitive to pMGL (Tan et al., 1997a). Additionally, no toxicity was detected at effective doses (as was determined by an absence of weight loss in the animals. Half-life in these experiments was determined to be only 2 hr as measured from collected blood samples. Additionally infusion of PLP is required in order to maintain MGL activity. In spite of the very short half-life, Tan et al. reported inhibition of tumor growth in comparison to a saline control.

Yang et al. studied the pharmacokinetics, the pharmacodymanics in terms of methionine depletion, the antigenicity, and toxicity of MGL in a primate model (Yang et al., 2004b). Dose-ranging studies were performed at 1000-4000 units/kg administered intravenously. The highest dose was able to reduce plasma methionine to an undetectable level (less than 0.5 µM) by 30 minutes after injection, with the methionine level remaining undetectable for 8 hr. Pharmacokinetic analysis showed that pMGL was eliminated with a half-life of 2.5 hr. An administration of that dose every 8 hr/day for 2 weeks resulted in a steady-state depletion of plasma methionine to less than 2 µM. Mild toxicity was observed through decreased food intake and slight weight loss. Unfortunately, re-challenge on day 28 resulted in anaphylactic shock and death in one animal indicating that pMGL is highly immunogenic, which is a significant disadvantage for human therapy. Subsequent pretreatment with hydrocortisone prevented the anaphylactic reaction, although vomiting was frequently observed. Additional re-challenges were carried out at days 66, 86, and 116. Anti-rMGL antibodies were detected after the first challenge, and increased in concentration for the duration of treatment.

In response to these observed obstacles to therapeutic implementation of MGL, Yang et al. studied the PEGylation of the enzyme and its effect on half-life and immunogenicity. The enzyme was coupled to methoxypolyethylene glycol succinimidyl glutarate (MEGC-PEG-5000). Dose ranging studies were again performed and 4,000 units/kg (90 mg/kg) was sufficient to reduce plasma methionine to <5 µmol/L for 12 hours. Pharmacokinetic analysis showed a 36 fold improvement in the serum clearance half-life of the PEGylated enzyme, as compared to the unpegylated. Pegylating also attenuated immunogenicity somewhat as only slight toxicities of decreased food intake and minor weight loss were observed. However the activity half-life was not improved as L-Met levels were only kept below detection levels for 12 hrs as opposed to 8 hrs for the unpegylated enzyme. These results, though promising in the ability of a L-Met depleting enzyme as an anti-neoplastic agent, are challenged by significant shortcomings of immunogenicity and pharmacokinetics.

Certain aspects of the present invention provide a modified cystathionine-γ-lyase with methionine degrading activity for treating diseases, such as tumor. Particularly, the modified polypeptide may have human polypeptide sequences and thus may prevent allergic reactions in human patients, allow repeated dosing, and increase the therapeutic efficacy.

Tumors for which the present treatment methods are useful include any malignant cell type such as those found in a solid tumor or a hematological tumor. Exemplary solid tumors can include, but are not limited to a tumor of an organ selected from the group consisting of pancreas, colon, cecum, stomach, brain, head, neck, ovary, kidney, larynx, sarcoma, lung, bladder, melanoma, prostate and breast. Exemplary hematological tumors include tumors of the bone marrow, T or B cell malignancies, leukemia, lymphomas, blastomas, myelomas, and the like.

The engineered human methioninase derived from cystathionase may be used herein as an antitumor agent in a variety of modalities for depleting methionine from a tumor cell, tumor tissue or the circulation of a mammal with cancer, or for depletion of methionine where its depletion is considered desirable.

Depletion can be conducted in vivo, in the circulation of a mammal, in vitro in cases where methionine depletion in tissue culture or other biological mediums is desired, and in ex vivo procedures where biological fluids, cells or tissues are manipulated outside the body and subsequently returned to the body of the patient mammal. Depletion of methionine from circulation, culture media, biological fluids or cells is conducted to reduce the amount of methionine accessible to the material being treated, and therefore comprises contacting the material to be depleted with a methionine-depleting amount of the engineered human methioninase under methionine-depleting conditions as to degrade the ambient methionine in the material being contacted.

Because tumor cells are dependent upon their nutrient medium for methionine, the depletion may be directed to the nutrient source for the cells, and not necessarily the cells themselves. Therefore, in an in vivo application, treating a tumor cell includes contacting the nutrient medium for a population of tumor cells with the engineered methioninase. In this embodiment, the medium can be blood, lymphatic fluid, spinal fluid and the like bodily fluid where methionine depletion is desired.

A methionine-depleting efficiency can vary widely depending upon the application, and typically depends upon the amount of methionine present in the material, the desired rate of depletion, and the tolerance of the material for exposure to methioninase. Methionine levels in a material, and therefore rates of methionine depletion from the material, can readily be monitored by a variety of chemical and biochemical methods well known in the art. Exemplary methionine-depleting amounts are described further herein, and can range from 0.001 to 100 units (U) of engineered methioninase, preferably about 0.01 to 10 U, and more preferably about 0.1 to 5 U engineered methioninase per milliliter (ml) of material to be treated.

Methionine-depleting conditions are buffer and temperature conditions compatible with the biological activity of a methioninase enzyme, and include moderate temperature, salt and pH conditions compatible with the enzyme, for example, physiological conditions. Exemplary conditions include about 4-40° C., ionic strength equivalent to about 0.05 to 0.2 M NaCl, and a pH of about 5 to 9, while physiological conditions are included.

In a particular embodiment, the invention contemplates methods of using engineered methioninase as an antitumor agent, and therefore comprises contacting a population of tumor cells with a therapeutically effective amount of engineered methioninase for a time period sufficient to inhibit tumor cell growth.

In one embodiment, the contacting in vivo is accomplished by administering, by intravenous or intraperitoneal injection, a therapeutically effective amount of a physiologically tolerable composition containing engineered methioninase of this invention to a patient, thereby depleting the circulating methionine source of the tumor cells present in the patient. The contacting of engineered methioninase can also be accomplished by administering the engineered methioninase into the tissue containing the tumor cells.

A therapeutically effective amount of an engineered methioninase is a predetermined amount calculated to achieve the desired effect, i.e., to deplete methionine in the tumor tissue or in a patient's circulation, and thereby cause the tumor cells to stop dividing. Thus, the dosage ranges for the administration of engineered methioninase of the invention are those large enough to produce the desired effect in which the symptoms of tumor cell division and cell cycling are reduced. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

For example, a therapeutically effective amount of an engineered methioninase may be an amount such that when administered in a physiologically tolerable composition is sufficient to achieve a intravascular (plasma) or local concentration of from about 0.001 to about 100 units (U) per ml, preferably above about 0.1 U, and more preferably above 1 U engineered methioninase per ml. Typical dosages can be administered based on body weight, and are in the range of about 5-1000 U/kilogram (kg)/day, preferably about 5-100 U/kg/day, more preferably about 10-50 U/kg/day, and more preferably about 20-40 U/kg/day.

The engineered methioninase can be administered parenterally by injection or by gradual infusion over time. The engineered methioninase can be administered intravenously, intraperitoneally, orally, intramuscularly, subcutaneously, intracavity, transdermally, dermally, can be delivered by peristaltic means, or can be injected directly into the tissue containing the tumor cells or can be administered by a pump connected to a catheter that may contain a potential biosensor or methionine.

The therapeutic compositions containing engineered methioninase are conventionally administered intravenously, as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of engineered methioninase and conversely low serum and tissue levels of methionine. Alternatively, continuous intravenous infusion sufficient to maintain concentrations in the blood in the ranges specified for in vivo therapies are contemplated.

IV. Conjugates

Compositions and methods of the present invention involve further modification of the engineered methioninase for improvement, such as by forming conjugates with heterologous peptide segments or polymers such as polyethylene glycol. In further aspects, the engineered methioninase may be linked to PEG to increase the hydrodynamic radius of the enzyme and hence increase the serum persistence. In certain aspects, the disclosed polypeptide may be conjugated to any targeting agent such as a ligand having the ability to specifically and stably bind to an external receptor or binding site on a tumor cell (U.S. Patent Publ. 2009/0304666)

A. Fusion Proteins

Certain embodiments of the present invention concern fusion proteins. These molecules may have the modified cystathionase linked at the N- or C-terminus to a heterologous domain. For example, fusions may also employ leader sequences from other species to permit the recombinant expression of a protein in a heterologous host. Another useful fusion includes the addition of a protein affinity tag like six histidine residues or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the modified cystathionine gamma-lyase may be linked to a peptide that increases the in vivo half-life, such as an XTEN polypeptide (Schellenberger el al., 2009).

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

B. Linkers

In certain embodiments, the engineered methioninase may be chemically conjugated using bifunctional cross-linking reagents or fused at the protein level with peptide linkers.

Bifunctional cross-linking reagents have been extensively used for a variety of purposes including preparation of affinity matrices, modification and stabilization of diverse structures, identification of ligand and receptor binding sites, and structural studies. Suitable peptide linkers may also be used to link the engineered methioninase, such as Gly-Ser linkers.

Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied.

A majority of heterobifunctional cross-linking reagents contains a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups.

Additionally, any other linking/coupling agents and/or mechanisms known to those of skill in the art may be used to combine human engineered methioninase, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo. These linkers are thus one group of linking agents.

In addition to hindered cross-linkers, non-hindered linkers also can be employed in accordance herewith. Other useful cross-linkers, not considered to contain or generate a protected disulfide, include SATA, SNP and 2-iminothiolane (Wawrzynczak & Thorpe, 1987). The use of such cross-linkers is well understood in the art. Another embodiment involves the use of flexible linkers.

Once chemically conjugated, the peptide generally will be purified to separate the conjugate from unconjugated agents and from other contaminants. A large number of purification techniques are available for use in providing conjugates of a sufficient degree of purity to render them clinically useful.

Purification methods based upon size separation, such as gel filtration, gel permeation or high performance liquid chromatography, will generally be of most use. Other chromatographic techniques, such as Blue-Sepharose separation, may also be used. Conventional methods to purify the fusion proteins from inclusion bodies may be useful, such as using weak detergents like sodium N-lauroyl-sarcosine (SLS).

C. Pegylation

In certain aspects of the invention, methods and compositions related to pegylation of engineered methioninase are disclosed. For example, the engineered methioninase may be pegylated in accordance with the methods disclosed herein.

Pegylation is the process of covalent attachment of poly (ethylene glycol) polymer chains to another molecule, normally a drug or therapeutic protein. Pegylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. Pegylation can also provide water solubility to hydrophobic drugs and proteins.

The first step of the pegylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates and carbonates. In the second generation pegylation chemistry more efficient functional groups such as aldehyde, esters, amides etc made available for conjugation.

As applications of pegylation have become more and more advanced and sophisticated, there has been an increase in need for heterobifunctional PEGs for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule (as shown in the example with PEG bis-vinylsulfone).

Proteins are generally PEGylated at nucleophilic sites such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has sonic drawbacks. The amide formed with the maleimides can be somewhat unstable under alkaline conditions so there may be some limitation to formulation options with this linker. The amide linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific pegylation at native cysteinyl residues is seldom carried out, since these residues are usually in the form of disulfide bonds or are required for biological activity. On the other hand, site-directed mutagenesis can be used to incorporate cysteinyl pegylation sites for thiol-specific linkers. The cysteine mutation must be designed such that it is accessible to the pegylation reagent and is still biologically active after pegylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the pegylation reaction difficult to control at large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific pegylation can be a challenge. Fortunately, because these reagents react with unprotonated amino groups, it is possible to direct the pegylation to lower-pK amino groups by performing the reaction at a lower pH. Generally the OK of the alpha-amino group is 1-2 pH units lower than the epsilon-amino group of lysine residues. By pegylating the molecule at pH 7 or below, high selectivity for the N-terminus frequently can be attained. However, this is only feasible if the N-terminal portion of the protein is not required for biological activity. Still, the pharmacokinetic benefits from pegylation frequently outweigh a significant loss of in vitro bioactivity, resulting in a product with much greater in vivo bioactivity regardless of pegylation chemistry.

There are several parameters to consider when developing a pegylation procedure. Fortunately, there are usually no more than four or five key parameters. The "design of experiments" approach to optimization of pegylation conditions can be very useful. For thiol-specific pegylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the pegylation reaction. For example, if the pegylation agent is only 70 percent active, the amount of PEG used should ensure that only active PEG molecules are counted in the protein-to-PEG reaction stoichiometry.

V. Proteins and Peptides

In certain embodiments, the present invention concerns novel compositions comprising at least one protein or peptide, such as engineered methioninase. These peptides may be comprised in a fusion protein or conjugated to an agent as described supra.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide are used interchangeably herein.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 1 below.

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology information's Genbank and GenPept databases (available on the world wide web at ncbi.nlm.nih.gov/). The coding regions for known genes may be amplified and/or expressed using the techniques disclosed herein or as would be known to those of ordinary skill in the art. Alternatively, various commercial preparations of proteins, polypeptides and peptides are known to those of skill in the art.

VI. Nucleic Acids and Vectors

In certain aspects of the invention, nucleic acid sequences encoding a an engineered methioninase or a fusion protein containing a modified cystathionase may be disclosed. Depending on which expression system to be used, nucleic acid sequences can be selected based on conventional methods. For example, the engineered methioninase is derived from human cystathionase and contains multiple codons that are rarely utilized in *E. coli* that may interfere with expression, therefore the respective genes or variants thereof may be codon optimized for *E. coli* expression. Various vectors may be also used to express the protein of interest, such as engineered methioninase. Exemplary vectors include, but are not limited, plasmid vectors, viral vectors, transposon or liposome-based vectors.

VII. Host Cells

Host cells may be any that may be transformed to allow the expression and secretion of engineered methioninase and conjugates thereof. The host cells may be bacteria, mammalian cells, yeast, or filamentous fungi. Various bacteria include *Escherichia* and *Bacillus*. Yeasts belonging to the genera *Saccharomyces, Kluyveromyces, Hansenula*, or *Pichia* would find use as an appropriate host cell. Various species of filamentous fungi may be used as expression hosts including the following genera: *Aspergillus, Trichoderma, Neurospora, Penicillium, Cephalosporium, Achlya, Podospora, Endothia, Mucor, Cochliobolus* and *Pyricularia*.

Examples of usable host organisms include bacteria, e.g., *Escherichia coli* MC1061, derivatives of *Bacillus subtilis* BRB1 (Sibakov et al., 1984), *Staphylococcus aureus* SAI123 (Lordanescu, 1975) or *Streptococcus lividans* (Hopwood et al., 1985); yeasts, e.g., *Saccharomyces cerevisiae* AH 22. (Mellor et al., 1983) and *Schizosaccharomyces pombe;* filamentous fungi, e.g., *Aspergillus nidulans, Aspergillus awamori* (Ward, 1989), *Trichoderma reesei* (Penttila et al., 1987; Harkki et al., 1989).

Examples of mammalian host cells include Chinese hamster ovary cells (CHO-K1; ATCC CCL61), rat pituitary cells (GH$_1$; ATCC CCL82), HeLa S3 cells (ATCC CCL2.2), rat hepatoma cells (H-4-II-E; Alt 1548) SV40-transformed monkey kidney cells (COS-1; ATCC CRL 1650) and murine embryonic cells (NIH-3T3; ATCC CRL 1658). The foregoing being illustrative but not limitative of the many possible host organisms known in the art. In principle, all hosts capable of secretion can be used whether prokaryotic or eukaryotic.

Mammalian host cells expressing the engineered methioninases and/or their fusion proteins are cultured under conditions typically employed to culture the parental cell line. Generally, cells are cultured in a standard medium containing physiological salts and nutrients, such as standard RPMI, MEM, IMEM or DMEM, typically supplemented with 5-10% serum, such as fetal bovine serum. Culture conditions are also standard, e.g., cultures are incubated at 37° C. in stationary or roller cultures until desired levels of the proteins are achieved.

VIII. Protein Purification

Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxyapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide always be provided in their most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments a protein or peptide may be isolated or purified, for example, an engineered methioninase, a fusion protein containing the engineered methioninase, or an engineered methioninase post pegylation. For example, a His tag or an affinity epitope may be comprised in such an engineered methioninase to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes such as proteins and industrial polymers. Typically, when an aqueous solution is used to transport the sample through the column, the technique is known as gel filtration chromatography, versus the name gel permeation chromatography which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or High pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

IX. Pharmaceutical Compositions

It is contemplated that the novel methioninase can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g. cancer that the surgery failed to eliminate) does not survive.

It is not intended that the present invention be limited by the particular nature of the therapeutic preparation. For example, such compositions can be provided in formulations together with physiologically tolerable liquid, gel or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Where clinical applications are contemplated, it may be necessary to prepare pharmaceutical compositions comprising proteins, antibodies and drugs in a form appropriate for the intended application. Generally, pharmaceutical compositions may comprise an effective amount of one or more cystathionase variants or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one cystathionase variant isolated by the method disclosed herein, or additional active ingredient will be known to those of skill in the art in light of the present disclosure, as exemplified by Remington's Pharmaceutical Sciences, $18^{th}$ Ed., 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, $18^{th}$ Ed., 1990, incorporated herein by reference). Except insofar as any conventional carrier is incompatible with the active ingredient, its use in the pharmaceutical compositions is contemplated.

Certain embodiments of the present invention may comprise different types of carriers depending on whether it is to be administered in solid, liquid or aerosol form, and whether it need to be sterile for such routes of administration as injection. The compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, $18^{th}$ Ed., 1990, incorporated herein by reference).

The modified polypeptides may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with certain aspects of the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include cystathionase variants, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the engineered methioninase or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

X. Kits

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of an engineered methioninase, optionally formulated as a pharmaceutical, or lyophilized, for use with a delivery device.

Kits may comprise a container with a label. Suitable containers include, for example, bottles, vials, and test tubes. The containers may be formed from a variety of materials such as glass or plastic. The container may hold a composition which includes an antibody that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

XI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Gene Synthesis and Expression of Native Human Cystathionine-γ-Lyase and Modified Human Cystathionine-γ-Lyase Using sequence and structural alignments of cystathionine-gamma-lyase (CGL) and methionine-γ-lyase (MGL) enzymes as a guide, CGL, particularly human CGL (hCGL) were converted to an enzyme for the efficient degrading of methionine.

The human cystathionase gene contains multiple codons that are rarely-utilized in E. coli and can interfere with expression. Thus, in order to optimize protein expression in E. coli, the hGCL gene was synthesized using codon optimized oligonucleotides designed using the DNA-Works software (Hoover et al., 2002). An NcoI 5' restriction site, an in-frame N-terminal His$_6$ tag and a 3' EcoRI site were introduced into the ORF. After cloning into a pET28a vector (Novagen), E. coli (BL21) transformants containing an appropriate cystathionase expression vector are grown at 37° C. using Terrific Broth (TB) media containing 50 µg/ml kanamycin in shake flasks at 250 rpm until reaching an OD$_{600}$ of 0.5-0.6. At this point the cultures are switched to a shaker at 25° C., induced with 0.5 mM IPTG, and allowed to express protein for an additional 12 hrs. Cell pellets are then collected by centrifugation and re-suspended in an IMAC (Immobilized Metal. Affinity Chromatography) buffer (10 mM NaPO$_4$/10 mM imidazole/300 mM NaCl, pH 8). After lysis by a French pressure cell, lysates were centrifuged at 20,000×g for 20 min at 4° C., and the resulting supernatant applied to a nickel IMAC column, washed with 10-20 column volumes of IMAC buffer, and then eluted with an IMAC elution buffer (50 mM NaPO$_4$/250 mkt imidazole/300 mM NaCl, pH 8). Fractions containing enzyme are then incubated with 10 mM pyridoxal-5'-phosphate (PLP) for an hour at 25° C. Using a 10,000 MWCO centrifugal filter device (Amicon), proteins are then buffer exchanged several times into a 100 mM PBS, 10% glycerol, pH 7.3 solution. Aliquots of cystathionase enzyme are then flash frozen in liquid nitrogen and stored at −80° C. Cystathionase purified in this manner is >95% homogeneous as assessed by SDS-PAGE and coomassie staining. The yield is calculated to be ~400 mg/L culture based upon the calculated extinction coefficient, $\varepsilon_{280}=29,870$ $M^{-1}cm^{-1}$ in a final buffer concentration of 6 M guanidinium hydrochloride, 20 mM phosphate buffer, pH 6.5 (Gill and von Hippel, 1989).

Example 2

96-Well Plate Screen for Methionine-γ-Lyase Activity and Ranking Clones

Both MGL and CGL produce 2-ketobutanoic acid from their respective substrates. A colorimetric assay for the detection of α-keto acids 3-methylbenzothiazolin-2-one hydrazone (MBTH) (Takakura et al., 2004) was scaled to a 96-well plate format for screening small libraries and for ranking clones with the greatest METase (methionine-γ-lyase) activity.

Single colonies encoding mutant enzymes displaying activity in the assay described in the preceding paragraph are picked into microwells in 96-well plates containing 75 µL of TB media/well and 50 µg/ml kanamycin. Cells are grown at 37° C. on a plate shaker until reaching an OD$_{600}$ of 0.8-1. After cooling to 25° C., an additional 75 µL of media/well containing 50 µg/ml kanamycin and 0.5 mM IPTG is added. Expression is performed at 25° C. with shaking for 2 hrs, following which 100 µL of culture/well is transferred to a 96 well assay plate. The assay plates are then centrifuged to pellet the cells, the media is removed, and the cells are lysed by addition of 50 µL/well of B-PER protein extraction reagent (Pierce). After clearing by centrifugation, the lysate is incubated with 5 mM L-Met at 37° C. for 10-12 hrs. The reaction is then derivatized by addition of 3 parts of 0.03% MBTH solution in 1 M sodium acetate pH 5. The plates are heated at 50° C. for 40 min and after cooling are read at 320 nm in a microliter plate reader.

Example 3

Genetic Selection for Methionine-γ-Lyase Activity

α-ketobutyrate is produced by the action of threonine deaminase (encoded by ilvA) in E. coli as the first enzyme in the isoleucine biosynthetic pathway. Almost 40 years ago, Grimminger and Feldner identified threonine deaminase mutants that were isoleucine auxotrophs (Grimminger and Feldner 1974) and more recently a threonine deaminase point mutant was found in a common expression strain BLR(DE3) that reportedly only has <5% of normal growth capacity when isoleucine is omitted from media (Goyer et al., 2007). Expression of methioninase, which produces α-ketobutyrate, was shown to rescue the growth of ilvA mutants and thus allow colony formation in minimal media. However, the threonine deaminase gene in BLR(DE3) is a point mutant, making reversion a distinct likelihood especially in very large libraries. Threonine deaminase is the distal gene in the isoleucine biosynthetic operon ilvGMEDA and is expressed as part of the operon or independently from an internal promoter (Lopes and Lawther 1989).

In order to avoid undesired effects on the expression of other Ile genes internal fragments within the 1545 bp ilvA gene of *E. coli* strain BL21 were deleted using *E. coli* strain JW3745-2 (Δ(araD-araB)567, ΔlacZ4787(::rrnB-3), λ-, rph-1, ΔilvA723::kan, Δ(rhaD-rhaB)568, hsdR514) obtained from the Yale *E. coli* Genetic Stock Center (New Haven, Conn.) through P1 transduction and curing of the kanamycin resistance marker by using the FLP recombinase plasmid pCP20 as described elsewhere (Datsenko and Wanner 2000). It has also been noted that L-cystathionine and L-homocysteine are intermediates in the *E. coli* methionine biosynthetic pathway (FIG. 11). L-cystathionine and L-homocysteine are substrates of cystathionine-γ-lyase that result in production of α-ketobutyrate and allow complementation of the isoleucine biosynthetic pathway. Therefore the gene metA (encoding homoserine-O-succinyltransferase) was knocked out using an *E. coli* strain JW3973-1 (Δ(araD-araB)567, ΔlacZ4787(::rrnB-3), λ-, rph-1, Δ(rhaD-rhaB)568, ΔmetA780::kan, hsdR514) obtained from the Yale *E. coli* Genetic Stock Center (New Haven, Conn.) through P1 transduction and curing of the kanamycin resistance marker by using the FLP recombinase plasmid pCP20 as described elsewhere (Datsenko and Wanner 2000). *E. coli* strain BL21 (DE3) (F- ompT gal dcm lon hsdSB (rB-mB-) λ(DE3 [lacI lacUV5-T7 gene 1 ind1 sam7 nin5]) was used as a recipient strain, resulting in an *E. coli* strain BL21(DE3) (ΔilvA, ΔmetA) which is auxotrophic for both L-isoleucine and L-methionine.

Thus *E. coli* BL21(DE3) (ΔilvA, ΔmetA)-harboring plasmids containing the genes for a methionine-γ-lyase, an engineered cystathionine-γ-lyase, can grow on M9-minimal media plates supplemented with L-methionine, but the same strain having only wild-type cystathionine-γ-lyase and an empty plasmid cannot (FIG. 12). Very large libraries of recombinantly expressed engineered cystathionine-γ-lyase variants that have methionine-γ-lyase activity can be thus be rapidly selected for against a background of inactive clones or clones with cystathionase activity. Larger colonies and those appearing more quickly are indicative of more active enzymes.

Example 4

Effect of Mutagenesis Upon Residues E59, R119, and E339 of hCGL

Structural analysis indicated that residues E59, R119, and E339 are likely involved in the recognition of hCGL for it substrate L-cystathionine. NNS codon saturation libraies were constructed at these sites and screened using the following mutagenic primers: (E59) Forward '5-ggccagcatagcggttttNNStatagccgtagcggc (SEQ ID NO:2), Reverse '5-GCCGCTACGGCTATASNNAAAACCGC-TATGCTGGCC (SEQ ID NO:3), (R119) Forward '5-gtatggtgggaccaatNNStatttccgtcaggtggcg (SEQ ID NO:4), Reverse '5-CGCCACCTGACGGAAATASNNAT-TGGTCCCACCATAC (SEQ ID NO:5), (E339) Forward '5-ctgaaactgtttaccctggcaNNSagcttgggcggctttg (SEQ ID NO:6), and Reverse '5-CAAAGCCGCC-CAAGCTSNNTGCCAGGGTAAACAGTTTCAG (SEQ ID NO:7), using the hCGL gene as template DNA and specific end primers; forward '5-gatataccATGGGAGGC-CATCACCACCATCATCATGGCGGGCAG-GAAAAGGATGCG (SEQ ID NO:8) and reverse '5-CTCGAATTCTCAACTGTGGCTTCCCGATGGGG-GATGGGCCGCTTTCAGCGCCTGATC C (SEQ ID NO:9). The PCR product was digested with NcoI and EcoRI and ligated into pET28a vector with T4 DNA ligase. The resulting ligations were transformed directly into *E. coli* (BL21) and plated on LB-kanamycin plates for subsequent screening as described in Example 2. Two times more colonies than the theoretical diversity of the libraries were screened. Clones displaying activity were isolated and the sequence of the hCGL gene was determined to identify the mutations.

The enzyme variants were purified to greater than 95% homogeneity as assessed by SDS-PAGE. Incubation with PLP was shown to enhance the specific activity presumably because the *E. coli* cells used for expression do not produce sufficient PLP for all the hCGL produced. Once the enzyme had been loaded with PLP it was stable with no loss of the cofactor upon storage.

Example 5

Characterization of Human Cystathionine-γ-Lyase Variants

Two hCGL variants identified from the screen as having the highest catalytic activity were found to have the following mutations: E59N or V, R119L, and E339V, as well as an N-terminal His6 tag addition. These variants were called hCGL-NLV (SEQ ID NO:10), and hCGL-VLV (SEQ ID NO:11) respectively. Both of these variants were characterized kinetically for their ability to degrade L-Met in a 100 mM PBS buffer at pH 7.3 and 37° C. using a 1 ml scale MBTH assay similar to that described in Example 2. The Ellman's reagent (DTNB) to detect release of methane thiol from hCGL, variant catalysis of L-Met, resulting in a facile continuous assay. Both hCGL-NLV, and hCGL-VLV had a $k_{cat}/K_M$ of ~1×10$^4$ s$^{-1}$ M$^{-1}$ for L-Met. The parent enzyme native hCGL was not able to degrade L-Met within the detection limits of these assays.

Figure 2:
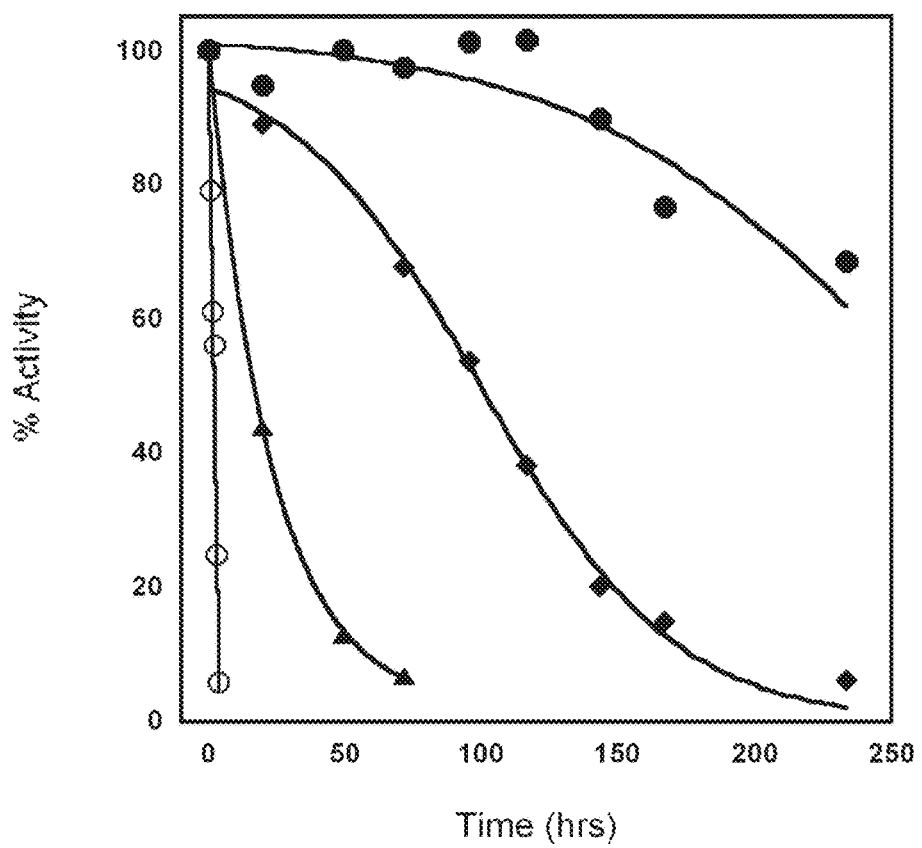
FIG. 2: Plot of % activity over time in pooled human serum incubated at 37° C. MGL from *P. putida* (○) with an apparent $T_{0.5}$ of 2±0.1 hrs, human CGL (▲) with an apparent $T_{0.5}$ of 16±0.8 hrs, variant hCGL-NLV (◆) with an apparent $T_{0.5}$ of 95±3 hrs, and variant hCGL-VLV (●) with an apparent $T_{0.5}$ of 260±18 hrs.

The serum stability of methionases was tested by incubating of the enzyme in pooled human serum at 37° C. and at a final concentration of 10 μM. At different time points, aliquots were withdrawn and tested for activity. After plotting the data the MGL from *P. putida* was found to have an apparent $T_{0.5}$ of 2±0.1 hrs. Human CGL showed an apparent $T_{0.5}$ of 16±0.8 hrs. Surprisingly, hCGL-NLV and CGL-VLV were dramatically more stable with the former showing an apparent $T_{0.5}$ of 95±3 hrs, and hCGL-VLV with an apparent $T_{0.5}$ of 260±18 hrs (FIG. 2).

Figure 3:
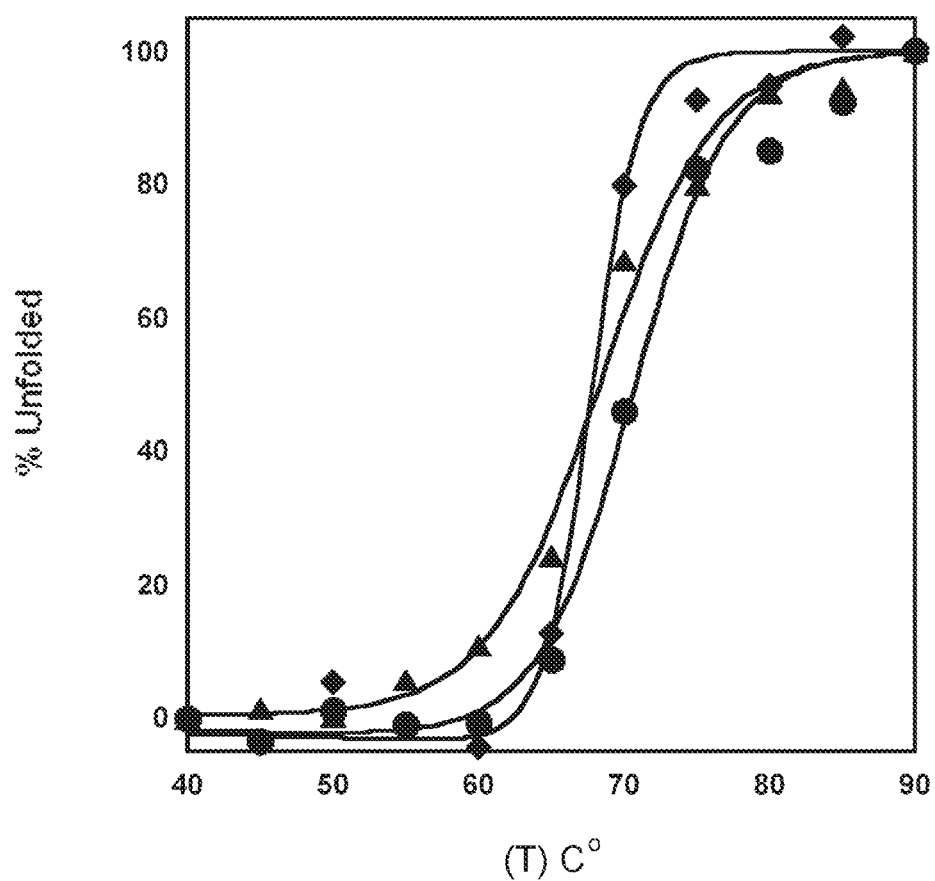
FIG. 3: Human CGL (▲) and variant hCGL-NLV (◆) with an apparent $T_M$ values of ~68° C., and variant hCGL-VLV (●) with an apparent $T_M$ of ~71° C.

The thermal stability of the methioninase enzymes was also evaluated by circular dichroism spectroscopy (CD). Human CGL and variant hCGL-NLV had apparent $T_M$ values of ~68° C., hCGL-VLV was slightly more stable with an apparent $T_M$ of ~71° C. (FIG. 3). The similar $T_M$ values of hCGL, hCGL-NLV, and hCGL-VLV suggests that the extended serum stability is due to the PLP cofactor being preferentially retained in the active-site of hCGL-NLV, and hCGL-VLV.

Example 6

Cytotoxicity of Human Methionine-γ-Lyase Against Neuroblastoma

Figure 6:
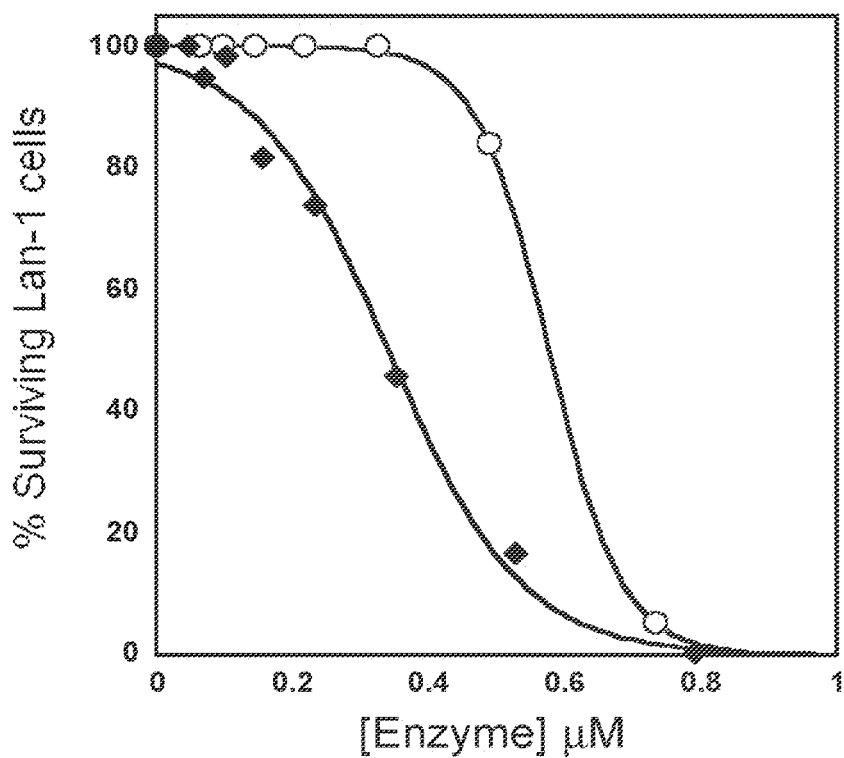
FIG. 6: Effect of L-Met depleting enzymes on neuroblastoma cell line Lan-1. Recombinant pMGL (○) with an apparent IC50 of 0.6 μM and recombinant hCGL-NLV (◆) with an apparent $IC_{50}$ of 0.3 μM.

The in vitro cytoxicity of hCGL and pMGL with the neuroblastoma cell line Lan-1 was evaluated. LAn-1 cells were seeded at ~7000 cells/well and incubated with varying concentrations of pMGL or hCGL-NLV. After 3-5 days exposure proliferation was measured using WST-8 previously and the data plotted to calculate apparent $IC_{50}$ values (Hu and Cheung 2009). Analysis of the resulting data (FIG. 6) yielded an apparent $IC_{50}$ value of 0.34 U/ml (~0.6 µM) for pMGL treated cells and an apparent $IC_{50}$ value of 0.15 U/ml (~0.3 µM) cells treated hCGL-NLV.

Example 7

Cytoxicity of PEGylated Human Methionine-γ-Lyase Against a Panel of Neuroblastoma Cell Lines In vitro proliferation of NB cell lines (BE(1)N, BE(2)N, BE(2)S, BE(2)C, SK-N-LD, NMB-7, SH-EP-1, IMR32, CHP-212, SKN-MM, LAN-1, LAI-66N, LAI-55N, LAI-5S) was assayed in 96-well plates (BD Biosciences, Bedford, Mass.) with varying concentrations of PEG-hMGL or PEG-hCGL-NLV.

Figure 9:
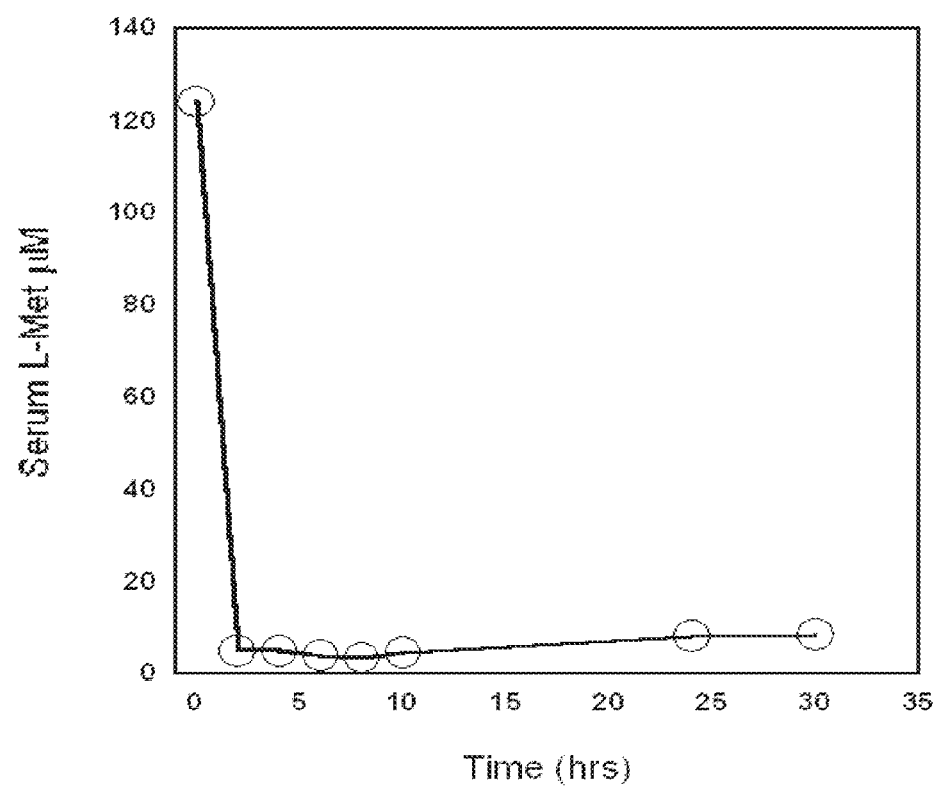
FIG. 9: Comparison of PEGylated hCGL-NLV with pMGL of the in vitro inhibition of proliferation of various neuroblastoma cell lines.

Twenty-four hours after seeding at a density of 3000-6000 cells/well, PEG-hCGL-NLV and pMGL were added. After 3 days of culture, PEG-hMGL and pMGL were removed, fresh medium added, and cells were incubated for another 36 hr. WST8 (Dojindo Molecular Technologies, Mass.) was added to culture wells at volume ratio of 1:10. After 4-6 hr of reaction, optical density (OD) was read at 450 nm. Cell proliferation was calculated as follows: % Cell Growth= ($OD_{450}$ of experimental well–$OD_{450}$ of medium-only well)/ ($OD_{450}$ of control well–$OD_{450}$ of medium-only well)× 100%. $IC_{50}$ (half maximal inhibitory drug concentration) was calculated using SigmaPlot 8.0 (Systat Software, Inc., San Jose, Calif.). PEG-hCGL-NLV showed cytoxicity against all cell lines tested with IC50 values ranging from 0.175-0.039 U similar to the pseudomonas MGL that had IC50 values ranging from 0.174-0.042 U (FIG. 9).

Example 8

Pharmacological Preparation of Human Cystathionine-γ-Lyase Variants hCGL-NLV was purified as described in Example 1 with one exception: after binding to the IMAC column, the protein is washed with extensively (90-100 column volumes) with an IMAC buffer containing 0.1% Triton 114 in the sample. 10-20 column volumes of IMAC buffer, and then eluted with an IMAC elution buffer (50 mM $NaPO_4$/ 250 mM imidazole/300 mM NaCl, pH 8). Wash with Triton 114 was employed to reduce endotoxin (lipopolysaccharide) contamination. The purified protein was subjected to buffer exchange into a 100 mM $NaPO_4$, buffer at pH 8.3 using a 10,000 MWCO filtration device (Amicon). Subsequently, PLP was added at a concentration of 10 mM and the protein was incubated for 1 hr at 25° C. Methoxy PEG Succinimidyl Carboxymethyl Ester 5000 MW (JenKem Technology) was then added to hCGL-NLV at a 80:1 molar ratio and allowed to react for 1 hr at 25° C. under constant stirring. The resulting mixture was extensively buffer exchanged (PBS with 10% glycerol) using a 100,000 MWCO filtration device (Amicon), and sterilized with a 0.2 micron syringe filter (VWR). All pegylated enzymes were analyzed for lipopolysaccharide (LPS) content using a Limulus Amebocyte Lysate (LAL) kit (Cape Cod Incorporated).

Figure 4:
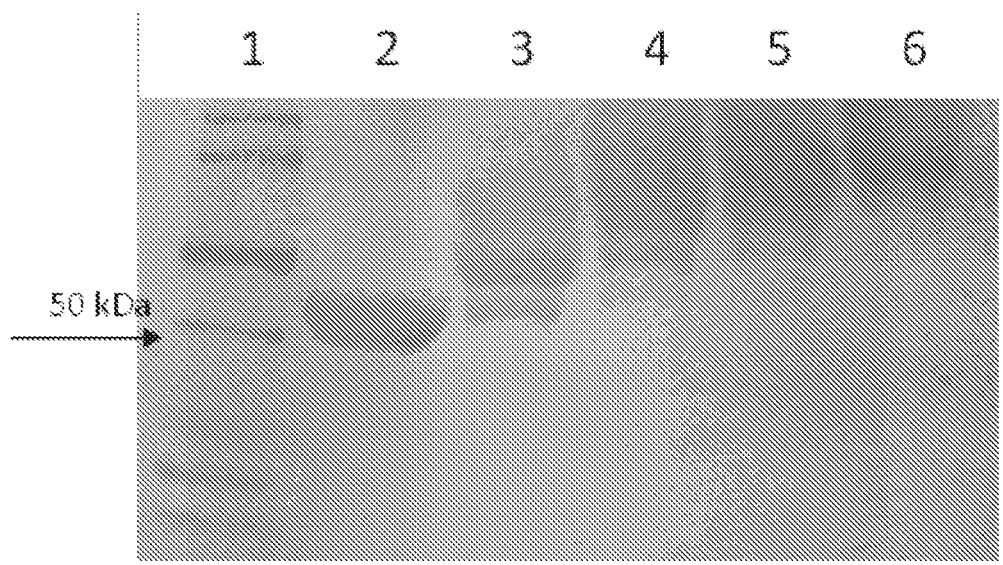
FIG. 4: PEGylation greatly increases the apparent molecular weight of hCGL variants. SDS-PAGE of MW ladder (lane 1), purified hCGL variant (lane 2), and purified hCGL variant modified with varying amounts of PEG NHS-ester MW 5000 (10, 20, 40 & 80 fold molar excess, lanes 3-6 respectively.
Figure 5:
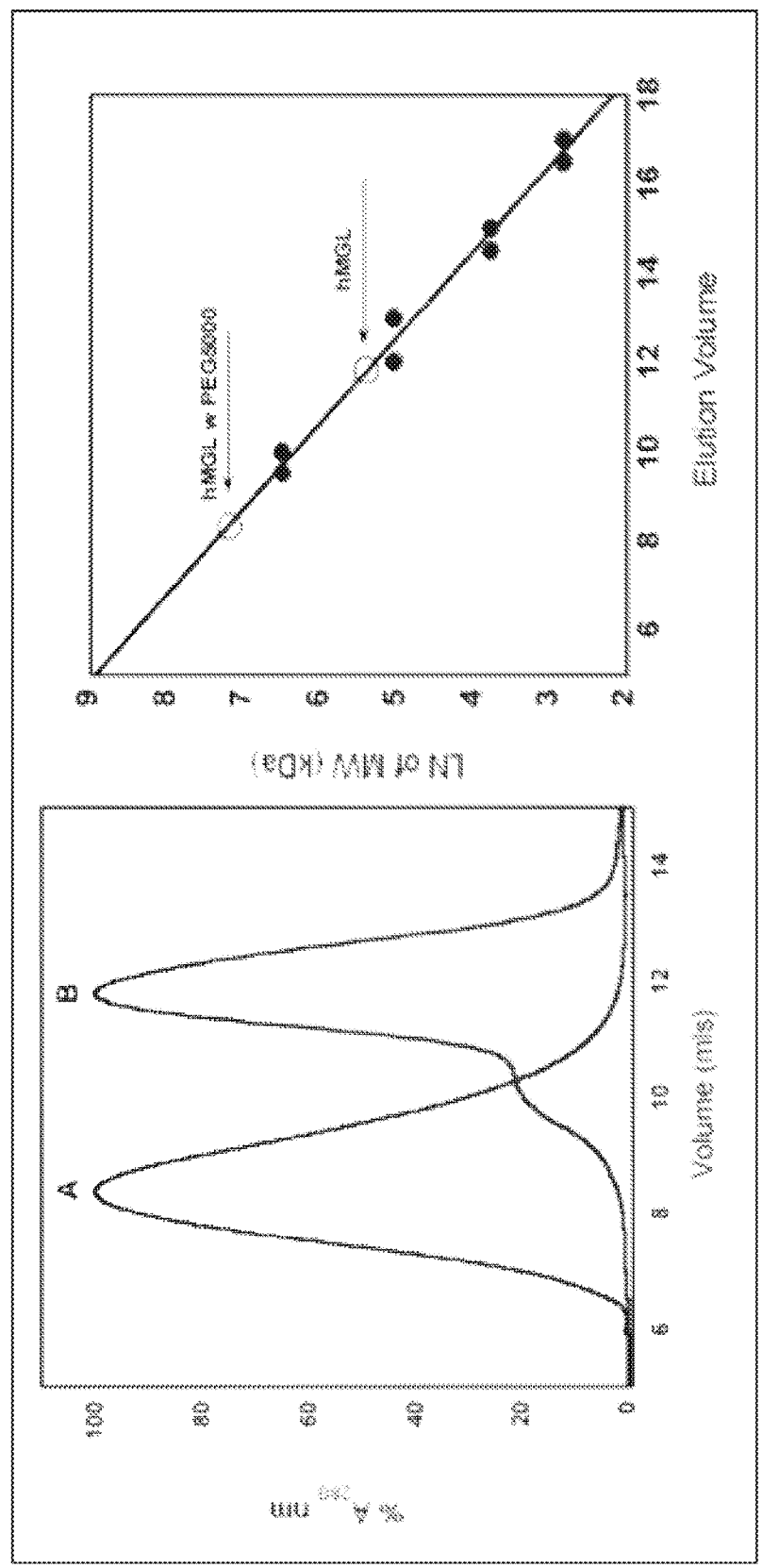
FIG. 5: PEGylation greatly increases the apparent molecular weight of hCGL variants. SEC (size exclusion chromatography) chromatography showing an apparent MW of ~1,340 kDa (A) for PEGylated hCGL variant and ~220 kDa for unpegylated hCGL variant (B).

Analysis by SDS-PAGE and size exclusion chromatography (FIGS. 4-5) shows that an 80 fold molar excess of PEG MW5000 greatly increases the hydrodynamic radius of hCGL variants with MGL activity from ~220 kDa for the unpegylated tetramer to an estimated 1,340 kDa for PEGylated hCGL variants. Pegylated human methionase was found to have nearly identical kinetic activity and in vitro serum stability as compared to the un-PEGylated enzyme.

Example 9

Pharmacodymanic Analysis of PEG MW 5000 hCGL-NLV in Mice

Figure 7:
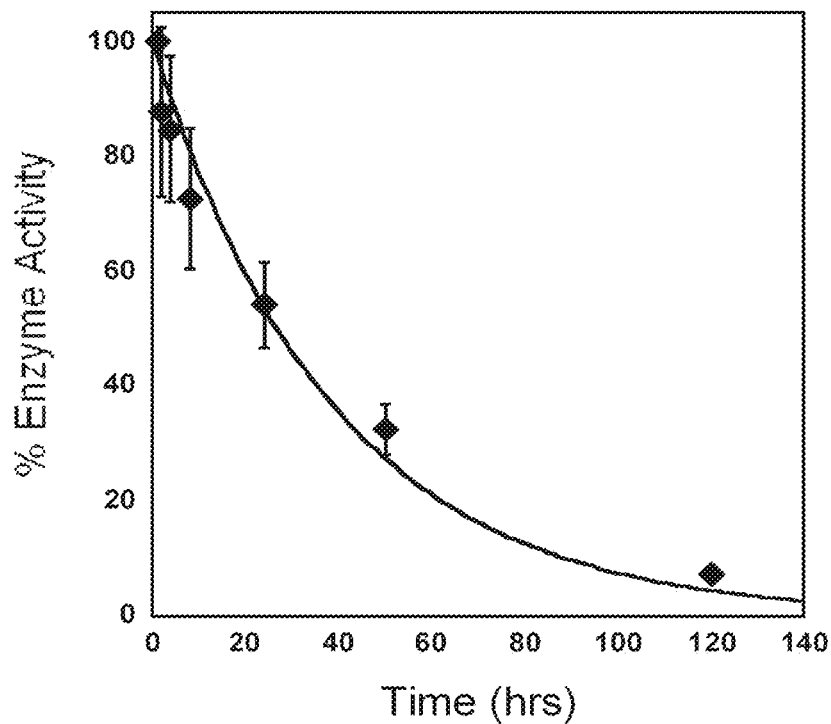
FIG. 7: Pharmacodynamic analysis of PEG-hCGL-NLV. The percentage of enzyme activity in serum samples relative to t=0 is plotted. (◆) over time with an apparent activity T1/2 of 28±4 hrs.

The in vivo half-life of PEGylated hCGL variants was determined in mice (balb/c) (n=5) following tail vein injection with 50 U of PEG-hCGL-NLV. Blood samples were withdrawn at different times and hCGL-NLV activity was determined as above. The activity in blood withdrawn at t=1 hr was set at 100%. An exponential fit to the data revealed a $T_{1/2}$ of 28±4 hrs (FIG. 7), a 14-fold improvement compared to PEG-pMGL.

Example 10

Methionine Depletion in Mouse Plasma

Mice (n=5) fed on a Methionine(-) Homocystine(-) Choline(-) (Met(-)Hcyss(-)Chl(-)) diet prior to treatment were dosed with 200 U of PEG-hCGL-NLV by tail vein injection. Plasma samples were analyzed for L-Met levels by HPLC basically as described elsewhere (Sun, et al. 2005). Blood methionine levels decreased from 124±37 µM prior to treatement to a minimum of 3.9±0.7 µM at 8 hrs and were kept low for over 24 hrs (FIG. 8).

Example 11

Effect of PEG-hCGL-NLV on LAN-1 Tumor Xenografts

Figure 10:
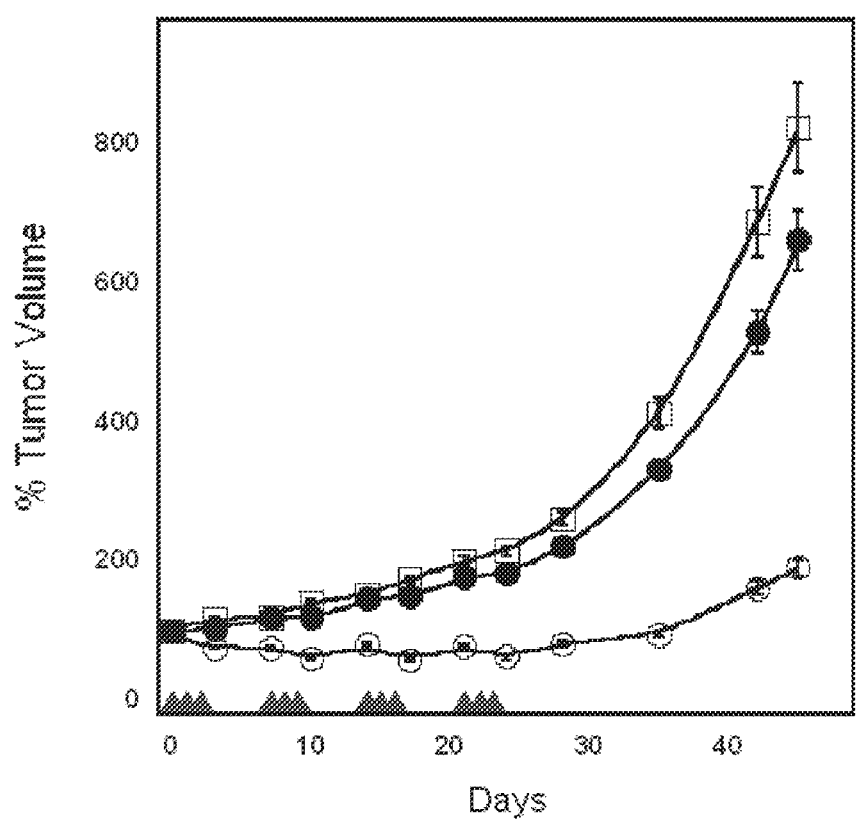
FIG. 10: Athymic mice bearing LAN-1 xenografts. (□) Control with normal diet (N=10); (●) Met(-)Hcyss(-)Chl(-) mouse feed (N=10), (○) 100 U PEG-hCGL-NLV in combination with Met(-)Hcyss(-)Chl(-) mouse feed (N=10) (▲ treatment days). Tumor growth rate was expressed as mean±SEM (standard error of the mean) for each group.

A schedule for PEG-hCGL-NLV administration was devised to minimize weight loss and maximize pharmacokinetics of PEG-hCGL-NLV. (The only dose limiting toxicity in vivo is weight loss after methionine deprivation.) When athymic mice xenografted with LAN-1 were treated with 100 Units PEG-hCGL-NLV i.v. thrice a week for 4 weeks, a 15-20% reversible weight loss was observed. 24 hr after the third PEG-hCGL-NLV injection during the last (4$^{th}$) week of treatment, plasma methionine concentrations were 5.8±2.1 µM among PEG-hCGL-NLV-treated mice fed with Met(-)Hcyss(-)Chl(-) diet, in contrast to 124±37 µM before treatment (n=10). Mice fed Met(-)Hcyss(-)Chl(-) diet had 10-15% reversible weight loss and the plasma methionine concentration was 13.2±4.5 µM while on Met(-)Hcyss (-)Chl(-) diet. When 100 Units PEG-hCGL-NLV treatment was combined with Met(-)Hcyss(-)Chl(-) diet, significant anti-tumor effect against LAN-1 xenografts (p<0.01) was observed when compared to the no treatment group or the group receiving only Met(-)Hcyss(-)Chl(-) diet (FIG. 10).

Example 12

Engineering of Primate Methione-γ-Lyases

The sequences of CGLs from primate species such as chimpanzees (*Pan troglodytes*), orangutans (*Pongo abelii*), and macaques (*Macaca fascicularis*) are respectively about 99, 96, and 95% identical in amino acid composition to human CGL. Primate CGL enzymes with mutations conferring Methionine-γ-lyase activity are constructed using standard mutagenesis techniques as described in Example 4. The resulting genes are cloned into pET28a Non-human primate hGCL with L-methionase activity are then expressed and purified as described above. Primate CGLs engineered with amino acid positions corresponding to N, or V59, L119, and V339 degrade L-Met with $k_{cat}/K_M$ values of at least $1\times10^2$ $s^{-1}M^{-1}$.

Examples of amino acid sequences of engineered primate CGLs with MGL activity are disclosed as below:

*Pongo abelii* CGL-NLV (SEQ ID NO:12, with V59N, R119L, and E339V substitutions and addition of an N-terminal His6 tag on the native sequence having Genbank ID NP_001124635.1 (i.e., SEQ ID NO:18)), *Pongo abelii* CGL-VLV (SEQ ID NO:13, with R119L and E339V substitutions and addition of an N-terminal His6 tag on the native sequence having Genbank ID NP_001124635.1);

*Macaca fascicularis* CGL-NLV (SEQ ID NO:14, with E59N, R119L, and E339V substitutions and addition of an N-terminal His6 tag on the native sequence having Genbank ID AAW71993.1 (i.e., SEQ ID NO:19)), *Macaca fascicularis* CGL-VLV (SEQ ID NO:15, with E59V, R119L, and E339V substitutions and addition of an N-terminal His6 tag on the native sequence having Genbank ID AAW71993.1);

*Pan Troglodytes* CGL-NLV (SEQ ID NO:16, with E59N, R119L, and E339V substitutions and addition of an N-terminal His6 tag on the native sequence having Genbank ID XP_513486.2 (i.e., SEQ ID NO:20)), and *Pan Troglodytes* CGL-VLV (SEQ ID NO:17, with E59V, R119L, and E339V substitutions and addition of an N-terminal His6 tag on the native sequence having Genbank ID XP_513486.2).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,889,155
U.S. Publn. 20090304666
Ashe et al., *Biochem. Biophys. Res. Commun.*, 57:417, 1974,
Ausubel et al., Current Protocols in Molecular Biology, Greene Publishing Associates and Wiley Interscience, N.Y., 1994.
Breillout et al., In: *Methionine dependency of malignant tumors: a possible approach for therapy*, Oxford University Press, 1628-1632, 1990
Datsenko and Wanner, *Proc. Nail Acad. Sci. USA*, 97(12): 6640-5, 2000.
Esaki and Soda, *Methods Enzymol.*, 143: 459, 1987.
Gill and von Hippel, *Anal. Biochem.*, 182:319-326, 1989.
Goyer et al., *Plant and cell Physiology*, 48(2):232, 2007.
Grimminger and Feidner, *J. Bacteriology*, 118(2):753, 1974.
Halpern et al., *Proc. Natl. Acad. Sci.*, 71:1133-1136, 1974.
Harkki et al., *BioTechnology*, 7:596-603, 1989.
Hoover et al., *J. Biol. Chem.*, 277:37647-37654, 2002.
Hopwood et al., In: *Genetic Manipulation of Streptomyces*, A Laboratory Manual, The John Innes Foundation, Norwich, Conn., 1985.
Hori et al., *Cancer Res.*, 56:2116-2122, 1996.
Hu and Cheung, *Intl. J. Cancer*, 124(7), 2009.
Ito et al., *J. Biochem.*, 79:1263, 1976.
Kreis and Goodenow, *Cancer Res.*, 38:2259-2262, 1978.
Kreis et al., *Cancer Res.*, 40:634-641, 1980.
Kreis, *Cancer Treatment Rpts.*, 63:1069, 1979.
Kudou et al., *J. Biochem.*, 141:535, 2007.
Lishko et al., *Anticancer Res.*, 13:1465-1468, 1993.
Lopes and Lawther, *Gene (Amsterdam)*, 76(2):255-269, 1989.
Lordanescu, *J. Bacteriol*, 12:597 601,1975.
Lu et al., *Biochem. Biophys. Res. Comm.*, 189:749-758, 1992.
Maniatis, et al., Molecular Cloning, A Laboratory Manual, Cold Spring Harbor Press, Cold Spring Harbor, N.Y., 1988.
Mellor et al., *Gene*, 24:1-14, 1983.
Nakamura et al., *Anal, Biochem.*, 138:421-424, 1984.
Penttila et al., *Gene*, 61:155-164,1987.
Rao et al., *J. Nutrition*, 120:837, 1990.
Remington's Pharmaceutical Sciences, 18th Ed. Mack Printing Company, 1289-1329, 1990.
Roopenian and Akilesh, *Nat. Rev. Immunol.*, 7:715-725, 2007.
Sibakov et al., *Eur. J. Biochem.*, 145:567 572, 1984.
Sridhar et al., Acta Crystall. Section D: Biolog, Crystall., 56:1665-1667, 2000.
Steegborn et al., *J. Biolog. Chem.*, 274:12675, 1999.
Sun et al., *Anticancer Res.*, 25(1A): 59-62, 2005.
Takakura et al., *Analytical Biochem.*, 327:233-240, 2004.
Tan et al., *Anticancer Res.*, 16:3937-3942, 1996a.
Tan et al., *Anticancer Res.*, 16:3931-3936, 1996b.
Tan et al., *Protein Express. Purif.*, 9:233-245, 1997a.
Tan et al., *Anticancer Res.*, 17:3857-3860, 2007b.
Volker Schellenbergerl, *Nature Biotech.*, 27:1186-1190, 2009.
Ward, Proc, Embo-Alko Workshop on Molecular Biology of Filamentous Fungi, Helsinki, 119-128, 1989.
Wawrzynczak & Thorpe, In: *Immunoconjugates, Antibody Conuugates In Radioimaging And Therapy Of Cancer*, Vogel (Ed.), NY, Oxford University Press, 28, 1987.
Yang et al., In: *PEGylation comers greatly extended half-lift and attenuated immunogenicity to recombinant methioninase in primates*, AACR, 6673-6678, 2004a.
Yang et al., In: *Pharmacokinetics, methionine depletion, and antigenicity of recombinant methioninase in primates*, AACR, 2131-2138, 2004b.
Yoshioka et al., *Cancer Res.*, 58:2583-2587, 1998.

What is claimed is:

1. A polypeptide comprising a primate cystathionine gamma-lyase variant comprising at least one amino acid substitution as compared to a native primate cystathionine gamma-lyase, wherein the cystathionine gamma-lyase variant has a catalytic specificity constant ($k_{cat}/K_M$) for degrading L-methionine between about 10 $M^{-1}s^{-1}$ and about ×10$^6$ $M^{-1}s^{-1}$ and wherein the at least one amino acid substitution comprises one or more of the following substitutions relative to SEQ ID NO: 1: E59V or E59N, R119L, and/or E339V.

2. The polypeptide of claim 1, wherein the at least one amino acid substitution comprises a R119L and E339V substitution.

3. The polypeptide of claim 2, wherein the at least one amino acid substitution further comprises an additional substitution of E59V or E59N.

4. The polypeptide of claim 1, wherein the cystathionine gamma-lyase variant has a $k_{cat}/K_M$ for degrading L-Methionine at least about $10^4 M^{-1}s^{-1}$.

5. The polypeptide of claim 4, wherein the cystathionine gamma-lyase variant has a $k_{cat}/K_M$ for degrading L-Homocystine lower than about 50 $M^{-1}s^{-1}$.

6. The polypeptide of claim 1, wherein the native primate cystathionine gamma-lyase has at least 95% sequence identity to the sequence of SEQ ID NO: 1.

7. The polypeptide of claim 6, wherein the native primate cystathionine gamma-lyase has at least 98% sequence identity to the sequence of SEQ ID NO: 1.

8. The polypeptide of claim 6, wherein the native primate cystathionine gamma-lyase has the sequence of any of SEQ ID NOs: 18-20.

9. The polypeptide of claim 6, wherein the native primate cystathionine gamma lyase is a human cystathionine gamma-lyase (SEQ ID NO: 1).

10. The polypeptide of claim 1, further comprising a heterologous peptide segment.

11. The polypeptide of claim 1, wherein the polypeptide is coupled to polyethylene glycol (PEG).

12. The polypeptide of claim 11, wherein the polypeptide is coupled to PEG via one or more Lys or Cys residues.

13. A nucleic acid comprising a nucleotide sequence encoding the polypeptide of claim 1.

14. The nucleic acid of claim 13, wherein the nucleic acid is codon optimized for expression in bacteria.

15. An expression vector comprising the nucleic acid of claim 14.

16. A host cell comprising the nucleic acid of claim 14.

17. The host cell of claim 16, wherein the host cell is bacteria.

18. The host cell of claim 17, wherein the host cell is an *E. coli* strain having deletions of genes ilvA and metA.

19. A pharmaceutical formulation comprising the polypeptide of claim 1 in a pharmaceutically acceptable carrier.

* * * * *

SEQUENCE LISTING

<160> NUMBER OF SEQ ID NOS: 20

<210> SEQ ID NO 1
<211> LENGTH: 405
<212> TYPE: PRT
<213> ORGANISM: Homo sapiens

<400> SEQUENCE: 1

```
Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365
```

```
Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 2
<211> LENGTH: 36
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(20)
<223> OTHER INFORMATION: n is a, c, g, or t

<400> SEQUENCE: 2
ggccagcata gcggttttnn statagccgt agcggc                              36

<210> SEQ ID NO 3
<211> LENGTH: 36
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(18)
<223> OTHER INFORMATION: n is a, c, g, or t

<400> SEQUENCE: 3
gccgctacgg ctatasnnaa aaccgctatg ctggcc                              36

<210> SEQ ID NO 4
<211> LENGTH: 37
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(18)
<223> OTHER INFORMATION: n is a, c, g, or t

<400> SEQUENCE: 4
gtatggtggg accaatnnst atttccgtca ggtggcg                             37

<210> SEQ ID NO 5
<211> LENGTH: 37
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(21)
<223> OTHER INFORMATION: n is a, c, g, or t

<400> SEQUENCE: 5
cgccacctga cggaaatasn nattggtccc accatac                             37

<210> SEQ ID NO 6
<211> LENGTH: 40
<212> TYPE: DNA
<213> ORGANISM: Artificial Sequence
```

<220> FEATURE:
<223> OTHER INFORMATION: Synthetic primer
<220> FEATURE:
<221> NAME/KEY: misc_feature
<222> LOCATION: (22)..(23)
<223> OTHER INFORMATION: n is a, c, g, or t

<400> SEQUENCE: 6
ctgaaactgt ttaccctggc annsagcttg ggcggctttg          40

<210> SEQ ID NO 7
<211> LENGTH: 40
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(19)
<223> OTHER INFORMATION: n is a, c, g, or t

<400> SEQUENCE: 7
caaagccgcc caagctsnnt gccagggtaa acagtttcag          40

<210> SEQ ID NO 8
<211> LENGTH: 56
<212> TYPE: DNA
<213> ORGANISM: Artificial Sequence
<220> FEATURE:
<223> OTHER INFORMATION: Synthetic primer

<400> SEQUENCE: 8
gatataccat gggaggccat caccaccatc atcatggcgg gcaggaaaag gatgcg          56

<210> SEQ ID NO 9
<211> LENGTH: 58
<212> TYPE: DNA
<213> ORGANISM: Artificial Sequence
<220> FEATURE:
<223> OTHER INFORMATION: Synthetic primer

<400> SEQUENCE: 9
ctcgaattct caactgtggc ttcccgatgg gggatgggcc gctttcagcg cctgatcc          58

<210> SEQ ID NO 10
<211> LENGTH: 415
<212> TYPE: PRT
<213> ORGANISM: Homo sapiens

<400> SEQUENCE: 10

Met Gly Gly His His His His His His Gly Gly Gln Glu Lys Asp Ala
1               5                   10                  15

Ser Ser Gln Gly Phe Leu Pro His Phe Gln His Phe Ala Thr Gln Ala
                20                  25                  30

Ile His Val Gly Gln Asp Pro Glu Gln Trp Thr Ser Arg Ala Val Val
            35                  40                  45

Pro Pro Ile Ser Leu Ser Thr Thr Phe Lys Gln Gly Ala Pro Gly Gln
        50                  55                  60

His Ser Gly Phe Asn Tyr Ser Arg Ser Gly Asn Pro Thr Arg Asn Cys
65                  70                  75                  80

Leu Glu Lys Ala Val Ala Ala Leu Asp Gly Ala Lys Tyr Cys Leu Ala
                85                  90                  95

Phe Ala Ser Gly Leu Ala Ala Thr Val Thr Ile Thr His Leu Leu Lys
                100                 105                 110

-continued

```
Ala Gly Asp Gln Ile Ile Cys Met Asp Asp Val Tyr Gly Thr Asn
            115                 120                 125

Leu Tyr Phe Arg Gln Val Ala Ser Glu Phe Gly Leu Lys Ile Ser Phe
130                 135                 140

Val Asp Cys Ser Lys Ile Lys Leu Leu Glu Ala Ala Ile Thr Pro Glu
145                 150                 155                 160

Thr Lys Leu Val Trp Ile Glu Thr Pro Thr Asn Pro Thr Gln Lys Val
                165                 170                 175

Ile Asp Ile Glu Gly Cys Ala His Ile Val His Lys His Gly Asp Ile
            180                 185                 190

Ile Leu Val Val Asp Asn Thr Phe Met Ser Pro Tyr Phe Gln Arg Pro
        195                 200                 205

Leu Ala Leu Gly Ala Asp Ile Ser Met Tyr Ser Ala Thr Lys Tyr Met
210                 215                 220

Asn Gly His Ser Asp Val Val Met Gly Leu Val Ser Val Asn Cys Glu
225                 230                 235                 240

Ser Leu His Asn Arg Leu Arg Phe Leu Gln Asn Ser Leu Gly Ala Val
                245                 250                 255

Pro Ser Pro Ile Asp Cys Tyr Leu Cys Asn Arg Gly Leu Lys Thr Leu
            260                 265                 270

His Val Arg Met Glu Lys His Phe Lys Asn Gly Met Ala Val Ala Gln
        275                 280                 285

Phe Leu Glu Ser Asn Pro Trp Val Glu Lys Val Ile Tyr Pro Gly Leu
290                 295                 300

Pro Ser His Pro Gln His Glu Leu Val Lys Arg Gln Cys Thr Gly Cys
305                 310                 315                 320

Thr Gly Met Val Thr Phe Tyr Ile Lys Gly Thr Leu Gln His Ala Glu
                325                 330                 335

Ile Phe Leu Lys Asn Leu Lys Leu Phe Thr Leu Ala Val Ser Leu Gly
            340                 345                 350

Gly Phe Glu Ser Leu Ala Glu Leu Pro Ala Ile Met Thr His Ala Ser
        355                 360                 365

Val Leu Lys Asn Asp Arg Asp Val Leu Gly Ile Ser Asp Thr Leu Ile
370                 375                 380

Arg Leu Ser Val Gly Leu Glu Asp Glu Glu Asp Leu Leu Glu Asp Leu
385                 390                 395                 400

Asp Gln Ala Leu Lys Ala Ala His Pro Pro Ser Gly Ser His Ser
                405                 410                 415

<210> SEQ ID NO 11
<211> LENGTH: 415
<212> TYPE: PRT
<213> ORGANISM: Homo sapiens

<400> SEQUENCE: 11

Met Gly Gly His His His His His Gly Gly Gln Glu Lys Asp Ala
1               5                   10                  15

Ser Ser Gln Gly Phe Leu Pro His Phe Gln His Phe Ala Thr Gln Ala
                20                  25                  30

Ile His Val Gly Gln Asp Pro Glu Gln Trp Thr Ser Arg Ala Val Val
            35                  40                  45

Pro Pro Ile Ser Leu Ser Thr Thr Phe Lys Gln Gly Ala Pro Gly Gln
        50                  55                  60

His Ser Gly Phe Val Tyr Ser Arg Ser Gly Asn Pro Thr Arg Asn Cys
65                  70                  75                  80
```

```
Leu Glu Lys Ala Val Ala Ala Leu Asp Gly Ala Lys Tyr Cys Leu Ala
                85                  90                  95

Phe Ala Ser Gly Leu Ala Ala Thr Val Thr Ile Thr His Leu Leu Lys
            100                 105                 110

Ala Gly Asp Gln Ile Ile Cys Met Asp Asp Val Tyr Gly Gly Thr Asn
            115                 120                 125

Leu Tyr Phe Arg Gln Val Ala Ser Glu Phe Gly Leu Lys Ile Ser Phe
        130                 135                 140

Val Asp Cys Ser Lys Ile Lys Leu Leu Glu Ala Ile Thr Pro Glu
145                 150                 155                 160

Thr Lys Leu Val Trp Ile Glu Thr Pro Thr Asn Pro Thr Gln Lys Val
                165                 170                 175

Ile Asp Ile Glu Gly Cys Ala His Ile Val His Lys His Gly Asp Ile
            180                 185                 190

Ile Leu Val Val Asp Asn Thr Phe Met Ser Pro Tyr Phe Gln Arg Pro
        195                 200                 205

Leu Ala Leu Gly Ala Asp Ile Ser Met Tyr Ser Ala Thr Lys Tyr Met
    210                 215                 220

Asn Gly His Ser Asp Val Val Met Gly Leu Val Ser Val Asn Cys Glu
225                 230                 235                 240

Ser Leu His Asn Arg Leu Arg Phe Leu Gln Asn Ser Leu Gly Ala Val
                245                 250                 255

Pro Ser Pro Ile Asp Cys Tyr Leu Cys Asn Arg Gly Leu Lys Thr Leu
            260                 265                 270

His Val Arg Met Glu Lys His Phe Lys Asn Gly Met Ala Val Ala Gln
        275                 280                 285

Phe Leu Glu Ser Asn Pro Trp Val Glu Lys Val Ile Tyr Pro Gly Leu
    290                 295                 300

Pro Ser His Pro Gln His Glu Leu Val Lys Arg Gln Cys Thr Gly Cys
305                 310                 315                 320

Thr Gly Met Val Thr Phe Tyr Ile Lys Gly Thr Leu Gln His Ala Glu
                325                 330                 335

Ile Phe Leu Lys Asn Leu Lys Leu Phe Thr Leu Ala Val Ser Leu Gly
            340                 345                 350

Gly Phe Glu Ser Leu Ala Glu Leu Pro Ala Ile Met Thr His Ala Ser
        355                 360                 365

Val Leu Lys Asn Asp Arg Asp Val Leu Gly Ile Ser Asp Thr Leu Ile
    370                 375                 380

Arg Leu Ser Val Gly Leu Glu Asp Glu Asp Leu Leu Glu Asp Leu
385                 390                 395                 400

Asp Gln Ala Leu Lys Ala Ala His Pro Pro Ser Gly Ser His Ser
                405                 410                 415

<210> SEQ ID NO 12
<211> LENGTH: 415
<212> TYPE: PRT
<213> ORGANISM: Pongo abelii

<400> SEQUENCE: 12

Met Gly Gly His His His His His His Gly Gly Gln Glu Lys Glu Ala
1               5                   10                  15

Ser Ser Gln Gly Phe Leu Pro His Phe Gln His Phe Ala Thr Gln Ala
            20                  25                  30

Ile His Val Gly Gln Glu Pro Glu Gln Trp Thr Ser Arg Ala Val Val
        35                  40                  45
```

-continued

Pro Pro Ile Ser Pro Ser Val Thr Phe Lys Gln Gly Ala Pro Gly Gln
                50                  55                  60

His Ser Gly Phe Asn Tyr Ser Arg Ser Gly Asn Pro Thr Arg Asn Cys
 65                  70                  75                  80

Leu Glu Lys Ala Val Ala Ala Leu Asp Gly Ala Lys Tyr Cys Leu Ala
                 85                  90                  95

Phe Ala Ser Gly Leu Ala Ala Thr Val Thr Ile Thr His Leu Leu Lys
                100                 105                 110

Ala Gly Asp Gln Ile Ile Cys Met Asp Asp Val Tyr Ala Gly Thr Asn
                115                 120                 125

Leu Tyr Phe Arg Gln Val Ala Ser Glu Phe Gly Leu Lys Ile Ser Phe
130                 135                 140

Val Asp Cys Ser Lys Ile Lys Leu Leu Glu Ala Ala Ile Thr Pro Glu
145                 150                 155                 160

Thr Lys Leu Val Trp Ile Glu Thr Pro Thr Asn Pro Thr Gln Lys Met
                165                 170                 175

Thr Asp Ile Glu Ala Cys Ala His Ile Val His Lys His Gly Asp Ile
                180                 185                 190

Ile Leu Val Val Asp Asn Thr Phe Met Ser Pro Tyr Phe Gln Arg Pro
                195                 200                 205

Leu Ala Leu Gly Ala Asp Ile Cys Met Cys Ser Ala Thr Lys Tyr Met
210                 215                 220

Asn Gly His Ser Asp Val Val Met Gly Leu Val Ser Val Asn Cys Glu
225                 230                 235                 240

Ser Leu Tyr Asn Arg Leu Arg Phe Leu Gln Asn Ser Leu Gly Ala Val
                245                 250                 255

Pro Ser Pro Ile Asp Cys Tyr Leu Cys Asn Arg Gly Leu Lys Thr Leu
                260                 265                 270

Gln Val Arg Met Glu Lys His Phe Lys Asn Gly Met Ala Val Ala Gln
                275                 280                 285

Phe Leu Glu Ser Asn Pro Trp Val Glu Lys Val Ile Tyr Pro Gly Leu
290                 295                 300

Pro Ser His Pro Gln His Glu Leu Val Lys Arg Gln Cys Thr Gly Cys
305                 310                 315                 320

Thr Gly Met Val Thr Phe Tyr Ile Lys Gly Thr Leu Gln His Ala Glu
                325                 330                 335

Ile Phe Leu Lys Asn Leu Lys Leu Phe Thr Leu Ala Val Ser Leu Gly
                340                 345                 350

Gly Phe Glu Ser Leu Val Glu Leu Pro Ala Val Met Thr His Ala Ser
                355                 360                 365

Val Leu Lys Lys Asp Arg Asp Val Leu Gly Ile Ser Asp Thr Leu Ile
370                 375                 380

Arg Leu Ser Val Gly Leu Glu Asp Glu Glu Asp Leu Leu Glu Asp Leu
385                 390                 395                 400

Asp Gln Ala Leu Lys Ala Ala His Pro Pro Ser Gly Ser His Ser
                405                 410                 415

<210> SEQ ID NO 13
<211> LENGTH: 415
<212> TYPE: PRT
<213> ORGANISM: Pongo abelii

<400> SEQUENCE: 13

```
Met Gly Gly His His His His His Gly Gly Gln Glu Lys Glu Ala
1               5                   10                  15

Ser Ser Gln Gly Phe Leu Pro His Phe Gln His Phe Ala Thr Gln Ala
            20                  25                  30

Ile His Val Gly Gln Glu Pro Glu Gln Trp Thr Ser Arg Ala Val Val
            35                  40                  45

Pro Pro Ile Ser Pro Ser Val Thr Phe Lys Gln Gly Ala Pro Gly Gln
50                  55                  60

His Ser Gly Phe Val Tyr Ser Arg Ser Gly Asn Pro Thr Arg Asn Cys
65                  70                  75                  80

Leu Glu Lys Ala Val Ala Ala Leu Asp Gly Ala Lys Tyr Cys Leu Ala
                85                  90                  95

Phe Ala Ser Gly Leu Ala Ala Thr Val Thr Ile Thr His Leu Leu Lys
            100                 105                 110

Ala Gly Asp Gln Ile Ile Cys Met Asp Asp Val Tyr Ala Gly Thr Asn
            115                 120                 125

Leu Tyr Phe Arg Gln Val Ala Ser Glu Phe Gly Leu Lys Ile Ser Phe
130                 135                 140

Val Asp Cys Ser Lys Ile Lys Leu Leu Glu Ala Ala Ile Thr Pro Glu
145                 150                 155                 160

Thr Lys Leu Val Trp Ile Glu Thr Pro Thr Asn Pro Thr Gln Lys Met
                165                 170                 175

Thr Asp Ile Glu Ala Cys Ala His Ile Val His Lys His Gly Asp Ile
            180                 185                 190

Ile Leu Val Val Asp Asn Thr Phe Met Ser Pro Tyr Phe Gln Arg Pro
            195                 200                 205

Leu Ala Leu Gly Ala Asp Ile Cys Met Cys Ser Ala Thr Lys Tyr Met
210                 215                 220

Asn Gly His Ser Asp Val Val Met Gly Leu Val Ser Val Asn Cys Glu
225                 230                 235                 240

Ser Leu Tyr Asn Arg Leu Arg Phe Leu Gln Asn Ser Leu Gly Ala Val
                245                 250                 255

Pro Ser Pro Ile Asp Cys Tyr Leu Cys Asn Arg Gly Leu Lys Thr Leu
            260                 265                 270

Gln Val Arg Met Glu Lys His Phe Lys Asn Gly Met Ala Val Ala Gln
            275                 280                 285

Phe Leu Glu Ser Asn Pro Trp Val Glu Lys Val Ile Tyr Pro Gly Leu
290                 295                 300

Pro Ser His Pro Gln His Glu Leu Val Lys Arg Gln Cys Thr Gly Cys
305                 310                 315                 320

Thr Gly Met Val Thr Phe Tyr Ile Lys Gly Thr Leu Gln His Ala Glu
                325                 330                 335

Ile Phe Leu Lys Asn Leu Lys Leu Phe Thr Leu Ala Val Ser Leu Gly
            340                 345                 350

Gly Phe Glu Ser Leu Val Glu Leu Pro Ala Val Met Thr His Ala Ser
            355                 360                 365

Val Leu Lys Lys Asp Arg Asp Val Leu Gly Ile Ser Asp Thr Leu Ile
370                 375                 380

Arg Leu Ser Val Gly Leu Glu Asp Glu Asp Leu Leu Glu Asp Leu
385                 390                 395                 400

Asp Gln Ala Leu Lys Ala Ala His Pro Pro Ser Gly Ser His Ser
                405                 410                 415
```

<210> SEQ ID NO 14
<211> LENGTH: 415
<212> TYPE: PRT
<213> ORGANISM: Macaca fascicularis

<400> SEQUENCE: 14

```
Met Gly Gly His His His His His Gly Gly Gln Glu Lys Asp Ala
1               5                   10                  15

Ser Ser Gln Gly Phe Leu Pro His Phe Gln His Phe Ala Thr Gln Ala
            20                  25                  30

Ile His Val Gly Gln Glu Pro Glu Gln Trp Thr Ser Arg Ala Val Val
        35                  40                  45

Pro Leu Ile Ser Leu Ser Thr Thr Phe Lys Gln Ala Ala Pro Gly Gln
50                  55                  60

His Ser Gly Phe Asn Tyr Ser Arg Ser Gly Asn Pro Thr Arg Asn Cys
65                  70                  75                  80

Leu Glu Lys Ala Val Ala Ala Leu Asp Gly Ala Lys Tyr Cys Leu Ala
                85                  90                  95

Phe Ala Ser Gly Leu Ala Ala Thr Val Thr Ile Thr His Leu Leu Lys
            100                 105                 110

Ala Gly Asp Gln Ile Ile Cys Met Asp Asp Val Tyr Gly Gly Thr Asn
        115                 120                 125

Leu Tyr Phe Arg Gln Val Ala Ser Glu Phe Gly Leu Lys Ile Ser Phe
130                 135                 140

Val Asp Cys Ser Lys Ile Lys Leu Leu Glu Ala Ala Ile Thr Pro Glu
145                 150                 155                 160

Thr Lys Leu Val Trp Ile Glu Thr Pro Thr Asn Pro Val Leu Lys Met
                165                 170                 175

Ile Asp Ile Glu Ala Cys Ala His Ile Val His Lys Arg Gly Asp Ile
            180                 185                 190

Ile Leu Val Val Asp Asn Thr Phe Met Ser Pro Tyr Phe Gln Arg Pro
        195                 200                 205

Leu Ala Leu Gly Ala Asp Ile Cys Met Cys Ser Ala Thr Lys Tyr Met
210                 215                 220

Asn Gly His Ser Asp Val Val Met Gly Leu Val Ser Val Asn Cys Glu
225                 230                 235                 240

Arg Leu His Asn Arg Leu Arg Phe Leu Gln Asn Ser Leu Gly Ala Val
                245                 250                 255

Pro Ser Pro Leu Asp Cys Tyr Leu Cys Asn Arg Gly Leu Lys Thr Leu
            260                 265                 270

His Val Arg Met Glu Lys His Phe Lys Asn Gly Met Ala Val Ala Gln
        275                 280                 285

Phe Leu Glu Ser Asn Pro Gly Val Glu Lys Val Ile Tyr Pro Gly Leu
290                 295                 300

Pro Ser His Pro Gln His Glu Leu Ala Lys Arg Gln Cys Thr Gly Cys
305                 310                 315                 320

Thr Gly Met Ile Thr Phe Tyr Ile Lys Gly Thr Leu Gln His Ala Glu
                325                 330                 335

Ile Phe Leu Lys Asn Leu Lys Leu Phe Thr Leu Ala Val Ser Leu Gly
            340                 345                 350

Gly Phe Glu Ser Leu Val Glu Leu Pro Ala Ile Met Thr His Ala Ser
        355                 360                 365

Val Pro Lys Asn Asp Arg Asp Val Leu Gly Ile Ser Asp Thr Leu Ile
370                 375                 380
```

```
Arg Leu Ser Val Gly Leu Glu Asp Glu Lys Asp Leu Leu Glu Asp Leu
385                 390                 395                 400

Asp Gln Ala Leu Lys Ala Ala His Pro Pro Ser Gly Ser His Asn
                405                 410                 415

<210> SEQ ID NO 15
<211> LENGTH: 415
<212> TYPE: PRT
<213> ORGANISM: Macaca fascicularis

<400> SEQUENCE: 15

Met Gly Gly His His His His His Gly Gly Gln Glu Lys Asp Ala
1               5                   10                  15

Ser Ser Gln Gly Phe Leu Pro His Phe Gln His Phe Ala Thr Gln Ala
                20                  25                  30

Ile His Val Gly Gln Glu Pro Glu Gln Trp Thr Ser Arg Ala Val Val
            35                  40                  45

Pro Leu Ile Ser Leu Ser Thr Thr Phe Lys Gln Ala Ala Pro Gly Gln
50                  55                  60

His Ser Gly Phe Val Tyr Ser Arg Ser Gly Asn Pro Thr Arg Asn Cys
65                  70                  75                  80

Leu Glu Lys Ala Val Ala Ala Leu Asp Gly Ala Lys Tyr Cys Leu Ala
                85                  90                  95

Phe Ala Ser Gly Leu Ala Ala Thr Val Thr Ile Thr His Leu Leu Lys
            100                 105                 110

Ala Gly Asp Gln Ile Ile Cys Met Asp Asp Val Tyr Gly Gly Thr Asn
        115                 120                 125

Leu Tyr Phe Arg Gln Val Ala Ser Glu Phe Gly Leu Lys Ile Ser Phe
130                 135                 140

Val Asp Cys Ser Lys Ile Lys Leu Leu Glu Ala Ala Ile Thr Pro Glu
145                 150                 155                 160

Thr Lys Leu Val Trp Ile Glu Thr Pro Thr Asn Pro Val Leu Lys Met
                165                 170                 175

Ile Asp Ile Glu Ala Cys Ala His Ile Val His Lys Arg Gly Asp Ile
            180                 185                 190

Ile Leu Val Val Asp Asn Thr Phe Met Ser Pro Tyr Phe Gln Arg Pro
        195                 200                 205

Leu Ala Leu Gly Ala Asp Ile Cys Met Cys Ser Ala Thr Lys Tyr Met
210                 215                 220

Asn Gly His Ser Asp Val Val Met Gly Leu Val Ser Val Asn Cys Glu
225                 230                 235                 240

Arg Leu His Asn Arg Leu Arg Phe Leu Gln Asn Ser Leu Gly Ala Val
                245                 250                 255

Pro Ser Pro Leu Asp Cys Tyr Leu Cys Asn Arg Gly Leu Lys Thr Leu
            260                 265                 270

His Val Arg Met Glu Lys His Phe Lys Asn Gly Met Ala Val Ala Gln
        275                 280                 285

Phe Leu Glu Ser Asn Pro Gly Val Glu Lys Val Ile Tyr Pro Gly Leu
290                 295                 300

Pro Ser His Pro Gln His Glu Leu Ala Lys Arg Gln Cys Thr Gly Cys
305                 310                 315                 320

Thr Gly Met Ile Thr Phe Tyr Ile Lys Gly Thr Leu Gln His Ala Glu
                325                 330                 335

Ile Phe Leu Lys Asn Leu Lys Leu Phe Thr Leu Ala Val Ser Leu Gly
            340                 345                 350
```

Gly Phe Glu Ser Leu Val Glu Leu Pro Ala Ile Met Thr His Ala Ser
                355                 360                 365

Val Pro Lys Asn Asp Arg Asp Val Leu Gly Ile Ser Asp Thr Leu Ile
    370                 375                 380

Arg Leu Ser Val Gly Leu Glu Asp Glu Lys Asp Leu Leu Glu Asp Leu
385                 390                 395                 400

Asp Gln Ala Leu Lys Ala Ala His Pro Pro Ser Gly Ser His Asn
                405                 410                 415

<210> SEQ ID NO 16
<211> LENGTH: 415
<212> TYPE: PRT
<213> ORGANISM: Pan troglodytes

<400> SEQUENCE: 16

Met Gly Gly His His His His His Gly Gly Gln Glu Lys Asp Ala
1               5                   10                  15

Ser Ser Gln Gly Phe Leu Pro His Phe Gln His Phe Ala Thr Gln Ala
                20                  25                  30

Ile His Val Gly Gln Asp Pro Glu Gln Trp Thr Ser Arg Ala Leu Val
            35                  40                  45

Pro Pro Ile Ser Leu Ser Thr Thr Phe Lys Gln Gly Ala Pro Gly Gln
    50                  55                  60

His Ser Gly Phe Asn Tyr Ser Arg Ser Gly Asn Pro Thr Arg Asn Cys
65              70                  75                  80

Leu Glu Lys Ala Val Ala Ala Leu Asp Gly Ala Lys Tyr Cys Leu Ala
                85                  90                  95

Phe Ala Ser Gly Leu Ala Ala Thr Val Thr Ile Thr His Leu Leu Lys
                100                 105                 110

Ala Gly Asp Gln Ile Ile Cys Met Asp Asp Val Tyr Gly Gly Thr Asn
            115                 120                 125

Leu Tyr Phe Arg Gln Val Ala Ser Glu Phe Gly Leu Lys Ile Ser Phe
    130                 135                 140

Val Asp Cys Ser Lys Ile Lys Leu Leu Glu Ala Ala Ile Thr Pro Glu
145                 150                 155                 160

Thr Lys Leu Val Trp Ile Glu Thr Pro Thr Asn Pro Thr Gln Lys Val
                165                 170                 175

Ile Asp Ile Glu Ala Cys Ala His Ile Val His Lys His Gly Asp Ile
            180                 185                 190

Ile Leu Val Val Asp Asn Thr Phe Met Ser Pro Tyr Phe Gln Arg Pro
    195                 200                 205

Leu Ala Leu Gly Ala Asp Ile Cys Met Tyr Ser Ala Thr Lys Tyr Met
210                 215                 220

Asn Gly His Ser Asp Val Val Met Gly Leu Val Ser Val Asn Cys Glu
225                 230                 235                 240

Ser Leu His Asn Arg Leu Arg Phe Leu Gln Asn Ser Leu Gly Ala Val
                245                 250                 255

Pro Ser Pro Ile Asp Cys Tyr Leu Cys Asn Arg Gly Leu Lys Thr Leu
            260                 265                 270

His Val Arg Met Glu Lys His Phe Lys Asn Gly Met Ala Val Ala Gln
    275                 280                 285

Phe Leu Glu Ser Asn Pro Trp Val Glu Lys Val Ile Tyr Pro Gly Leu
    290                 295                 300

Pro Ser His Pro Gln His Glu Leu Val Lys Arg Gln Cys Thr Gly Cys
305                 310                 315                 320

```
Thr Gly Met Val Thr Phe Tyr Ile Lys Gly Thr Leu Gln His Ala Glu
            325                 330                 335

Ile Phe Leu Lys Asn Leu Lys Leu Phe Thr Leu Ala Val Ser Leu Gly
        340                 345                 350

Gly Phe Glu Ser Leu Ala Glu Leu Pro Ala Ile Met Thr His Ala Ser
            355                 360                 365

Val Leu Lys Asn Asp Arg Asp Val Leu Gly Ile Ser Asp Thr Leu Ile
370                 375                 380

Arg Leu Ser Val Gly Leu Glu Asp Glu Asp Leu Leu Glu Asp Leu
385                 390                 395                 400

Asp Gln Ala Leu Lys Ala Ala His Pro Pro Ser Gly Ser His Ser
                405                 410                 415

<210> SEQ ID NO 17
<211> LENGTH: 415
<212> TYPE: PRT
<213> ORGANISM: Pan troglodytes

<400> SEQUENCE: 17

Met Gly Gly His His His His His Gly Gly Gln Glu Lys Asp Ala
1               5                   10                  15

Ser Ser Gln Gly Phe Leu Pro His Phe Gln His Phe Ala Thr Gln Ala
            20                  25                  30

Ile His Val Gly Gln Asp Pro Glu Gln Trp Thr Ser Arg Ala Leu Val
        35                  40                  45

Pro Pro Ile Ser Leu Ser Thr Thr Phe Lys Gln Gly Ala Pro Gly Gln
    50                  55                  60

His Ser Gly Phe Val Tyr Ser Arg Ser Gly Asn Pro Thr Arg Asn Cys
65                  70                  75                  80

Leu Glu Lys Ala Val Ala Ala Leu Asp Gly Ala Lys Tyr Cys Leu Ala
                85                  90                  95

Phe Ala Ser Gly Leu Ala Ala Thr Val Thr Ile Thr His Leu Leu Lys
            100                 105                 110

Ala Gly Asp Gln Ile Ile Cys Met Asp Asp Val Tyr Gly Gly Thr Asn
        115                 120                 125

Leu Tyr Phe Arg Gln Val Ala Ser Glu Phe Gly Leu Lys Ile Ser Phe
130                 135                 140

Val Asp Cys Ser Lys Ile Lys Leu Leu Glu Ala Ala Ile Thr Pro Glu
145                 150                 155                 160

Thr Lys Leu Val Trp Ile Glu Thr Pro Thr Asn Pro Thr Gln Lys Val
                165                 170                 175

Ile Asp Ile Glu Ala Cys Ala His Ile Val His Lys His Gly Asp Ile
            180                 185                 190

Ile Leu Val Val Asp Asn Thr Phe Met Ser Pro Tyr Phe Gln Arg Pro
        195                 200                 205

Leu Ala Leu Gly Ala Asp Ile Cys Met Tyr Ser Ala Thr Lys Tyr Met
    210                 215                 220

Asn Gly His Ser Asp Val Val Met Gly Leu Val Ser Val Asn Cys Glu
225                 230                 235                 240

Ser Leu His Asn Arg Leu Arg Phe Leu Gln Asn Ser Leu Gly Ala Val
                245                 250                 255

Pro Ser Pro Ile Asp Cys Tyr Leu Cys Asn Arg Gly Leu Lys Thr Leu
            260                 265                 270

His Val Arg Met Glu Lys His Phe Lys Asn Gly Met Ala Val Ala Gln
        275                 280                 285
```

```
Phe Leu Glu Ser Asn Pro Trp Val Glu Lys Val Ile Tyr Pro Gly Leu
    290                 295                 300
Pro Ser His Pro Gln His Glu Leu Val Lys Arg Gln Cys Thr Gly Cys
305                 310                 315                 320
Thr Gly Met Val Thr Phe Tyr Ile Lys Gly Thr Leu Gln His Ala Glu
                325                 330                 335
Ile Phe Leu Lys Asn Leu Lys Leu Phe Thr Leu Ala Val Ser Leu Gly
            340                 345                 350
Gly Phe Glu Ser Leu Ala Glu Leu Pro Ala Ile Met Thr His Ala Ser
        355                 360                 365
Val Leu Lys Asn Asp Arg Asp Val Leu Gly Ile Ser Asp Thr Leu Ile
    370                 375                 380
Arg Leu Ser Val Gly Leu Glu Asp Glu Asp Leu Leu Glu Asp Leu
385                 390                 395                 400
Asp Gln Ala Leu Lys Ala Ala His Pro Pro Ser Gly Ser His Ser
            405                 410                 415

<210> SEQ ID NO 18
<211> LENGTH: 405
<212> TYPE: PRT
<213> ORGANISM: Pongo abelii

<400> SEQUENCE: 18

Met Gln Glu Lys Glu Ala Ser Ser Gln Gly Phe Leu Pro His Phe Gln
1               5                   10                  15
His Phe Ala Thr Gln Ala Ile His Val Gly Gln Glu Pro Glu Gln Trp
            20                  25                  30
Thr Ser Arg Ala Val Val Pro Pro Ile Ser Pro Ser Val Thr Phe Lys
        35                  40                  45
Gln Gly Ala Pro Gly Gln His Ser Gly Phe Val Tyr Ser Arg Ser Gly
    50                  55                  60
Asn Pro Thr Arg Asn Cys Leu Glu Lys Ala Val Ala Ala Leu Asp Gly
65                  70                  75                  80
Ala Lys Tyr Cys Leu Ala Phe Ala Ser Gly Leu Ala Ala Thr Val Thr
                85                  90                  95
Ile Thr His Leu Leu Lys Ala Gly Asp Gln Ile Ile Cys Met Asp Asp
            100                 105                 110
Val Tyr Ala Gly Thr Asn Arg Tyr Phe Arg Gln Val Ala Ser Glu Phe
        115                 120                 125
Gly Leu Lys Ile Ser Phe Val Asp Cys Ser Lys Ile Lys Leu Leu Glu
    130                 135                 140
Ala Ala Ile Thr Pro Glu Thr Lys Leu Val Trp Ile Glu Thr Pro Thr
145                 150                 155                 160
Asn Pro Thr Gln Lys Met Thr Asp Ile Glu Ala Cys Ala His Ile Val
                165                 170                 175
His Lys His Gly Asp Ile Ile Leu Val Val Asp Asn Thr Phe Met Ser
            180                 185                 190
Pro Tyr Phe Gln Arg Pro Leu Ala Leu Gly Ala Asp Ile Cys Met Cys
        195                 200                 205
Ser Ala Thr Lys Tyr Met Asn Gly His Ser Asp Val Val Met Gly Leu
    210                 215                 220
Val Ser Val Asn Cys Glu Ser Leu Tyr Asn Arg Leu Arg Phe Leu Gln
225                 230                 235                 240
Asn Ser Leu Gly Ala Val Pro Ser Pro Ile Asp Cys Tyr Leu Cys Asn
                245                 250                 255
```

```
Arg Gly Leu Lys Thr Leu Gln Val Arg Met Glu Lys His Phe Lys Asn
                260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
        290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Val Glu Leu Pro Ala
            340                 345                 350

Val Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 19
<211> LENGTH: 405
<212> TYPE: PRT
<213> ORGANISM: Macaca fascicularis

<400> SEQUENCE: 19

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220
```

-continued

```
Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
            245                 250                 255

Arg Gly Leu Lys Thr Leu His Val Arg Met Glu Lys His Phe Lys Asn
        260                 265                 270

Gly Met Ala Val Ala Gln Phe Leu Glu Ser Asn Pro Gly Val Glu Lys
    275                 280                 285

Val Ile Tyr Pro Gly Leu Pro Ser His Pro Gln His Glu Leu Ala Lys
290                 295                 300

Arg Gln Cys Thr Gly Cys Thr Gly Met Ile Thr Phe Tyr Ile Lys Gly
305                 310                 315                 320

Thr Leu Gln His Ala Glu Ile Phe Leu Lys Asn Leu Lys Leu Phe Thr
            325                 330                 335

Leu Ala Glu Ser Leu Gly Gly Phe Glu Ser Leu Val Glu Leu Pro Ala
        340                 345                 350

Ile Met Thr His Ala Ser Val Pro Lys Asn Asp Arg Asp Val Leu Gly
    355                 360                 365

Ile Ser Asp Thr Leu Ile Arg Leu Ser Val Gly Leu Glu Asp Glu Lys
370                 375                 380

Asp Leu Leu Glu Asp Leu Asp Gln Ala Leu Lys Ala Ala His Pro Pro
385                 390                 395                 400

Ser Gly Ser His Asn
            405

<210> SEQ ID NO 20
<211> LENGTH: 405
<212> TYPE: PRT
<213> ORGANISM: Pan troglodytes

<400> SEQUENCE: 20

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
            85                  90                  95

Ile Thr His Leu Leu Lys Ala Gly Asp Gln Ile Ile Cys Met Asp Asp
        100                 105                 110

Val Tyr Gly Gly Thr Asn Arg Tyr Phe Arg Gln Val Ala Ser Glu Phe
    115                 120                 125

Gly Leu Lys Ile Ser Phe Val Asp Cys Ser Lys Ile Lys Leu Leu Glu
130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
            165                 170                 175

His Lys His Gly Asp Ile Ile Leu Val Val Asp Asn Thr Phe Met Ser
        180                 185                 190
```

-continued

```
Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Met Gly Leu
        210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
                260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
        290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Ala Glu Leu Pro Ala
                340                 345                 350

Ile Met Thr His Ala Ser Val Leu Lys Asn Asp Arg Asp Val Leu Gly
                355                 360                 365

Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser
                405
```